United States Patent [19]
Brendel et al.

[11] Patent Number: 6,015,822
[45] Date of Patent: Jan. 18, 2000

[54] SULFONAMIDE-SUBSTITUTED FUSED 5-MEMBERED RING COMPOUNDS, THEIR USE AS A MEDICAMENT, AND PHARMACEUTICAL PREPARATIONS COMPRISING THEM

[75] Inventors: Joachim Brendel, Bad Vilbel; Uwe Gerlach, Hattersheim; Hans Jochen Lang, Hofheim; Klaus Weidmann, Kronberg, all of Germany

[73] Assignee: Hoechst Marion Roussel Deutschland GmbH, Frankfurt am Main, Germany

[21] Appl. No.: 09/188,181

[22] Filed: Nov. 9, 1998

[30] Foreign Application Priority Data

Nov. 10, 1997 [DE] Germany .................. 197 49 453

[51] Int. Cl.⁷ .................. A61K 31/44; C07D 213/42
[52] U.S. Cl. .................. 514/357; 514/601; 546/338; 564/98
[58] Field of Search .................. 564/98; 514/601, 514/357; 546/338

[56] References Cited

U.S. PATENT DOCUMENTS

| | | | |
|---|---|---|---|
| 4,929,754 | 5/1990 | Nickl et al. | 562/428 |
| 5,639,913 | 6/1997 | Lidor et al. | 564/304 |
| 5,877,218 | 3/1999 | Herzig et al. | 514/617 |
| 5,877,221 | 3/1999 | Cohen et al. | 514/629 |
| 5,880,159 | 3/1999 | Herzig et al. | 514/625 |

FOREIGN PATENT DOCUMENTS

| | | |
|---|---|---|
| 0253321 | 1/1988 | European Pat. Off. . |
| 0 315 009 | 5/1989 | European Pat. Off. . |
| 0 370 901 | 5/1990 | European Pat. Off. . |
| 0 389 861 | 10/1990 | European Pat. Off. . |
| 2135999A | 9/1984 | United Kingdom . |

*Primary Examiner*—Joseph K. McKane
*Attorney, Agent, or Firm*—Finnegan, Henderson, Farabow, Garrett & Dunner, L.L.P.

[57] ABSTRACT

Compounds of the formula I

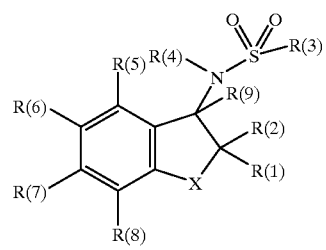

having the meanings of the substituents indicated in the claims are outstandingly active substances for the production of medicaments for the prophylaxis and for the therapy of cardiovascular disorders, in particular arrhythmias, for the treatment of ulcers of the gastro-intestinal region or for the treatment of diarrheal illnesses.

23 Claims, No Drawings

SULFONAMIDE-SUBSTITUTED FUSED 5-MEMBERED RING COMPOUNDS, THEIR USE AS A MEDICAMENT, AND PHARMACEUTICAL PREPARATIONS COMPRISING THEM

Sulfonamide-substituted fused 5-membered ring compounds, their use as a medicament, and pharmaceutical preparations comprising them The invention relates to compounds of the formula I

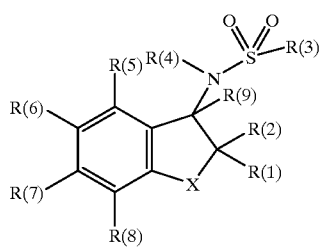

in which R(1), R(2), R(3), R(4), R(5), R(6), R(7), R(8), R(9) and X have the meanings indicated in the following, their preparation and their use, in particular in pharmaceuticals. The compounds affect the potassium channel opened by cyclic adenosine monophosphate (cAMP) or the $I_{Ks}$ channel and are outstandingly suitable as pharmaceutically active compounds, for example for the prophylaxis and therapy of cardiovascular diseases, in particular arrhythmias, for the treatment of ulcers of the gastrointestinal region or for the treatment of diarrheal illnesses.

In pharmaceutical chemistry, the class of the 4-acylaminochroman derivatives has been worked on intensively in recent years. The most prominent representative of this class is cromakalim of the formula A (J. Med. Chem. 1986, 29, 2194). In addition, homologous compounds, such as indan B (J. Med. Chem. 1991, 34, 919), which is derived by ring constriction of the pyran ring, have been synthesized and studied.

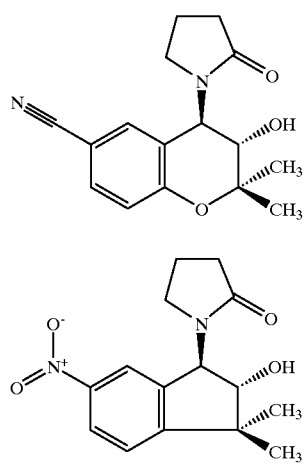

Cromakalim and other related 4-acylaminochroman derivatives or 1-acylaminoindan derivatives are compounds having a relaxant action on smooth muscular organs, so that they are used for lowering raised blood pressure as a result of vascular muscle relaxation and in the treatment of asthma as a result of the relaxation of the smooth musculature of the airways. It is common to all these preparations that they act at the cellular level, for example, of smooth muscle cells and lead there to an opening of specific ATP-sensitive $K^+$ channels. The increase in negative charge in the cell (hyperpolarization) induced by the efflux of $K^+$ ions counteracts via secondary mechanisms the increase in the intracellular $Ca^{2+}$ concentration and thus cell activation which leads, for example, to muscle contraction.

The compounds of the formula I according to the invention differ structurally from these acylamino derivatives, inter alia, by the replacement of the acylamino group by a sulfonylamino function. While cromakalim (formula A) and analogous acylamino compounds (e.g. compound B) act as openers of ATP-sensitive $K^+$ channels, the compounds of the formula I according to the invention having the sulfonylamino structure, however, do not show any opening action on this $K^+$ (ATP) channel, but surprisingly show a strong and specific blocking (closing) action on a $K^+$ channel which is opened by cyclic adenosine monophosphate (cAMP) and differs fundamentally from the $K^+$ (ATP) channel mentioned. More recent investigations show that this $K^+$ (cAMP) channel identified in colonic tissue is very similar, perhaps even identical, to the $I_{Ks}$ channel identified in the cardiac muscle. In fact, it was possible, for the compounds of the formula I according to the invention, to show a strong blocking action on the $I_{Ks}$ channel in guinea pig cardiomyocytes and on the $I_{sK}$ channel expressed in Xenopus oocytes. As a result of this blocking of the $K^+$ (cAMP) channel or of the $I_{Ks}$ channel, the compounds according to the invention display pharmacological actions of high therapeutic utility in the living body.

In addition to the abovementioned cromakalim or acylaminochroman derivatives, compounds having 4-sulfonylaminochroman structure are described in the literature, but these compounds differ significantly both in the structure and in the biological activity from the compounds of the formula I according to the invention. Thus, EP-A-315 009 describes chroman derivatives having 4-phenylsulfonylamino structure and having antithrombotic and antiallergic properties. EP-A-389 861 and JP 01294677 describe 3-hydroxychroman and chromene derivatives having a cyclic 4-sulfonylamino group (for example compound C), respectively, which are said to act as antihypertensive agents via an activation of the $K^+$ (ATP) channel. EP-A-370 901 describes 3-hydroxychroman and chromene derivatives having a 4-sulfonylamino group where the remaining valency of the nitrogen atom carries a hydrogen atom, and having CNS action. Further 4-sulfonylamino chroman derivatives are described in Bioorg. Med. Chem. Lett. 4 (1994), 769–773: "N-sulfonamides of benzopyran-related potassium channel openers: conversion of glyburyde insensitive smooth muscle relaxants to potent smooth muscle contractors", and also in FEBS Letters 396 (1996), 271–275: "Specific blockade of slowly activating $I_{sK}$ channels by chromanols . . . " and Pflügers Arch.—Eur. J. Physiol. 429 (1995), 517–530: "A new class of inhibitors of cAMP-mediated Cl-secretion in rabbit colon, acting by the reduction of cAMP-activated $K^+$ conductance".

[Structure C shown at top]

The present invention relates to compounds of the formula I

[Structure I shown]

in which:
R(1) and R(2) independently of one another are hydrogen, CF$_3$, alkyl having 1, 2, 3, 4, 5 or 6 carbon atoms;
or
R(2) and R(9) together are a bond;
or R(2) is —OR(10a), if X is —CR(22)R(23)—;
R(10a) is hydrogen, acetyl or alkyl having 1, 2 or 3 carbon atoms;
R(3) is R(10b)—C$_n$H$_{2n}$—NR(11)— or R(10b)—C$_n$H$_{2n}$—, where a CH$_2$ group in the C$_n$H$_2$n group is unchanged or is replaced by —O—, —CO—, —S—, —SO—, —SO$_2$— or —NR(12a)—;
R(12a) is hydrogen, methyl or ethyl;
R(10b) is methyl, cycloalkyl having 3, 4, 5, 6, 7 or 8 carbon atoms, CF$_3$, C$_2$F$_5$ or C$_3$F$_7$;
n is zero, 1, 2, 3, 4, 5, 6, 7, 8, 9 or 10;
R(11) is hydrogen or alkyl having 1, 2, 3, 4, 5 or 6 carbon atoms; or
R(10b) and R(11) together are a bond if n is greater than 2;
or
R(3) together with R(4) is an alkylene chain having 3, 4, 5, 6, 7 or 8 carbon atoms, where a CH$_2$ group of the alkylene chain is unchanged or is replaced by —O—, —CO—, —S—, —SO—, —SO$_2$— or —NR(12a)—;
R(12a) is hydrogen, methyl or ethyl;
R(4) is R(13)—C$_r$H$_{2r}$, where a CH$_2$ group of the C$_r$H$_{2r}$ group is unchanged or is replaced by —O—, —CH=CH—, —C≡C—, —CO—, —CO—O—, —O—CO—, —S—, —SO—, —SO$_2$—, —NR(14)— or —CONR(14)—;
R(14) is hydrogen, alkyl having 1, 2 or 3 carbon atoms, —C$_y$H$_{2y}$—OR(12b), —C$_y$H$_{2y}$—NR(12b)$_2$;
R(12b) is hydrogen, methyl or ethyl;
y is 2 or 3;
R(13) is CH$_3$, CF$_3$, C$_2$F$_5$, C$_3$F$_7$, cycloalkyl having 3, 4, 5, 6, 7 or 8 carbon atoms, —NR(15)R(16), —CONR(15)R(16), —OR(17), —COOR(17), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents, selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(15) and R(16) independently of one another, are hydrogen or alkyl having 1, 2, 3 or 4 carbon atoms;
or
R(15) and R(16) together are a chain of 4 or 5 methylene groups of which one CH$_2$ group is unchanged or is replaced by —O—, —S—, —NH—, —N(CH$_3$)— or —N(benzyl)-;
R(17) is hydrogen, alkyl having 1, 2 or 3 carbon atoms, —C$_z$H$_{2z}$OR(12c);
R(12c) is hydrogen, methyl or ethyl;
z is 2 or 3;
r is zero, 1, 2, 3, 4, 5, 6, 7, 8, 9, 10, 11, 12, 13, 14, 15, 16, 17, 18, 19 or 20;
R(5), R(6), R(7) and R(8) independently of one another are hydrogen, F, Cl, Br, I, alkyl having 1, 2, 3, 4 or 5 carbon atoms, cycloalkyl having 3, 4, 5, 6, 7 or 8 carbon atoms, —CN, —CF$_3$, —C$_2$F$_5$, —C$_3$F$_7$, —N$_3$, —NO$_2$, —Y—C$_s$H$_{2s}$—R(18), phenyl, thienyl, furyl or a nitrogen-containing heterocycle having 1, 2, 3, 4, 5, 6, 7, 8 or 9 carbon atoms, where phenyl, thienyl, furyl and the nitrogen-containing heterocycle are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
Y is —O—, —CO—, —CO—O—, —O—CO—, —S—, —SO—, —SO$_2$—, —O—SO$_2$—, —SO$_2$NR(10c)— or —CONR(10c)—, where the link to the phenyl group is in each case effected through the atom on the left;
R(10c) is hydrogen or alkyl having 1, 2 or 3 carbon atoms;
s is zero, 1, 2, 3, 4, 5 or 6;
R(18) is hydrogen, methyl, CF$_3$, C$_2$F$_5$, C$_3$F$_7$, cycloalkyl having 3, 4, 5, 6, 7 or 8 carbon atoms, —OR(21), —COOR(21), —NR(15a)R(16a), —CONR(15a)R(16a), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(15a) and R(16a) independently of one another, are hydrogen or alkyl having 1, 2, 3 or 4 carbon atoms; or
R(15a) and R(16a) together are a chain of 4 or 5 methylene groups of which one CH$_2$ group is unchanged or is replaced by —O—, —S—, —NH—, —N(CH$_3$)— or —N(benzyl)-;
R(21) is hydrogen or alkyl having 1, 2 or 3 carbon atoms;
R(9) is hydrogen or together with R(2) is a bond;
X is —CR(22)R(23)—, —O—, —NR(24)—, —S—, —SO—, —SO$_2$—;
R(22) and R(23) independently of one another are hydrogen, CF$_3$, alkyl having 1, 2, 3, 4, 5 or 6 carbon atoms;
R(24) is hydrogen, alkyl having 1, 2, 3, 4, 5 or 6 carbon atoms or phenyl which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

or their physiologically tolerable salts.

In the foregoing definition of Y, the phrase "where the link to the phenyl group is in each case effected through the atom on the left" means, in the case of a single atom, through that atom. For example, with —O—, the link to the phenyl group is effected through the O atom. Otherwise, the link to the phenyl group is effected through the atom furthest left. For example, with —$SO_2$NR(10c)—, the link to the phenyl group is effected through the S atom.

The present invention also relates to processes for preparing a compound of the formula I, to a pharmaceutical composition comprising said compound, together with a pharmaceutically acceptable carrier, and to the therapeutic treatment and/or prophylaxis of various syndromes with said compound or composition. Additional features and advantages of the invention are set forth in the description that follows, and, in part, will be apparent from the description or may be learned from practice of the invention. The advantages of the invention will be realized and attained by the compounds, processes, pharmaceutical compositions, therapeutic treatments and/or prophylaxes of various syndromes particularly pointed out in the written description and claims.

Both the foregoing general description and the following detailed description of the invention are exemplary and explanatory only and are not restrictive of the claimed invention.

Preference is given to compounds of the formula I in which:

R(1) is hydrogen;

R(2) is hydrogen or —OR(10a);
  R(10a) is hydrogen, acetyl or alkyl having 1, 2 or 3 carbon atoms;

or

R(2) and R(9) together are a bond;
  R(3) is R(10b)—$C_nH_{2n}$—NR(11)— or R(10b)—$C_nH_{2n}$—, where a $CH_2$ group in the $C_nH_{2n}$ group is unchanged or is replaced by —O—, —CO—, —S—, —SO—, —$SO_2$— or —NR(12a)—;
  R(12a) is hydrogen, methyl or ethyl;
  R(10b) is methyl, cycloalkyl having 3, 4, 5, 6, 7 or 8 carbon atoms, $CF_3$, $C_2F_5$ or $C_3F_7$;
  n is zero, 1, 2, 3, 4, 5, 6, 7, 8, 9 or 10;
  R(11) is hydrogen or alkyl having 1, 2, 3, 4, 5 or 6 carbon atoms; or
  R(10b) and R(11) together are a bond if n is greater than 2;

or

R(3) together with R(4) is an alkylene chain having 3, 4, 5, 6, 7 or 8 carbon atoms, where a $CH_2$ group of the alkylene chain is unchanged or is replaced by —O—, —CO—, —S—, —SO—, —$SO_2$— or —NR(12a)—;
  R(12a) is hydrogen, methyl or ethyl;
  R(4) is R(13)—$C_rH_{2r}$, where a $CH_2$ group of the $C_rH_{2r}$ group is unchanged or is replaced by —O—, —CH=CH—, —C≡C—, —CO—, —CO—O—, —O—CO—, —S—, —SO—, —$SO_2$—, —NR(14)— or —CONR(14)—;
  R(14) is hydrogen, alkyl having 1, 2 or 3 carbon atoms, —$C_yH_{2y}$—OR(12b), —$C_yH_{2y}$—NR(12b)$_2$;
  R(12b) is hydrogen, methyl or ethyl;
  y is 2 or 3;

R(13) is $CH_3$, $CF_3$, $C_2F_5$, $C_3F_7$, cycloalkyl having 3, 4, 5, 6, 7 or 8 carbon atoms, —NR(15)R(16), —CONR(15)R(16), —OR(17), —COOR(17), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, l, $CF_3$, $NO_2$, CN, $NH_2$, OH, methyl, ethyl, methoxy, dimethylamino, sulfamoyl, methylsulfonyl and methylsulfonylamino;
  R(15) and R(16) independently of one another are hydrogen or alkyl having 1, 2, 3 or 4 carbon atoms; or
  R(15) and R(16) together are a chain of 4 or 5 methylene groups of which one $CH_2$ group is unchanged or is replaced by —O—, —S—, —NH—, —N($CH_3$)— or -N(benzyl)-;
  R(17) is hydrogen, alkyl having 1, 2 or 3 carbon atoms, —$C_zH_{2z}$—OR(12c);
  R(12c) is hydrogen, methyl or ethyl;
  z is 2 or 3;
  r is zero, 1, 2, 3, 4, 5, 6, 7, 8, 9, 10, 11, 12, 13, 14, 15, 16, 17, 18, 19 or 20;

R(5), R(6), R(7) and R(8) independently of one another are hydrogen, F, Cl, Br, l, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Y—$C_sH_{2s}$—R(18), phenyl, thienyl, furyl or a nitrogen-containing heterocycle having 1, 2, 3, 4, 5, 6, 7, 8 or 9 carbon atoms, where phenyl, thienyl, furyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
  Y is —O—, —CO—, —CO—O—, —O—CO—, —S—, —SO—, —$SO_2$—, —O—$SO_2$—, —$SO_2$NR(10c) or —CONR(10c)—, where the link to the phenyl group is in each case effected through the atom on the left; R(10c) is hydrogen or alkyl having 1, 2 or 3 carbon atoms;
  s is zero, 1, 2, 3, 4, 5 or 6;
  R(18) is hydrogen, methyl, $CF_3$, $C_2F_5$, $C_3F_7$, cycloalkyl having 3, 4, 5, 6, 7 or 8 carbon atoms, —OR(21), —COOR(21), —NR(15a)R(16a), —CONR(15a)R(16a), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
  R(15a) and R(16a) independently of one another are hydrogen or alkyl having 1, 2, 3 or 4 carbon atoms; or
  R(15a) and R(16a) together are a chain of 4 or 5 methylene groups of which one $CH_2$ group is unchanged or is replaced by —O—, —S—, —NH—, —N($CH_3$)— or -N(benzyl)-;
  R(21) is hydrogen or alkyl having 1, 2 or 3 carbon atoms;

R(9) is hydrogen or together with R(2) is a bond;

X is —CR(22)R(23)—;
  R(22) and R(23) independently of one another are hydrogen, $CF_3$, alkyl having 1, 2, 3, 4, 5 or 6 carbon atoms;

or their physiologically tolerable salts.

Particular preference is given to compounds of the formula I in which:

R(1) is hydrogen;

R(2) is hydrogen or —OR(10a);
   R(10a) is hydrogen, acetyl or alkyl having 1, 2 or 3 carbon atoms;

or

R(2) and R(9) together are a bond;

R(3) is R(10b)—$C_nH_{2n}$—,
   R(10b) is methyl, cycloalkyl having 3, 4, 5 or 6 carbon atoms, $CF_3$, $C_2F_5$ or $C_3F_7$;
   n is zero, 1, 2, 3, 4 or 5;

R(4) is R(13)—$C_rH_{2r}$, where a $CH_2$ group of the $C_rH_{2r}$ group is unchanged or is replaced by —O—, —CO—, —CO—O—, —O—CO—, —NR(14)— or —CONR(14)—;
   R(14) is hydrogen, alkyl having 1, 2 or 3 carbon atoms, —$C_yH_{2y}$—OR(12b), —$C_yH_{2y}$—NR(12b)$_2$;
   R(12b) is hydrogen, methyl or ethyl;
   y is 2 or 3;
   R(13) is $CH_3$, $CF_3$, $C_2F_5$, $C_3F_7$, cycloalkyl having 3, 4, 5 or 6 carbon atoms, —NR(15)R(16), —CONR(15)R(16), —OR(17), —COOR(17), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, $NH_2$, OH, methyl, ethyl, methoxy, dimethylamino, sulfamoyl, methylsulfonyl and methylsulfonylamino;
   R(15) and R(16) independently of one another are hydrogen or alkyl having 1, 2, 3 or 4 carbon atoms; or
   R(15) and R(16) together are a chain of 4 or 5 methylene groups of which one $CH_2$ group is unchanged or is replaced by —O—, —S—, —NH—, —N(CH$_3$)— or -N(benzyl)-;
   R(17) is hydrogen or alkyl having 1, 2 or 3 carbon atoms;
   r is zero, 1, 2, 3, 4, 5, 6, 7, 8, 9 or 10;

R(5), R(6), R(7) and R(8) independently of one another are hydrogen, F, Cl, Br, alkyl having 1, 2, 3, 4 or 5 carbon atoms, cycloalkyl having 3, 4, 5 or 6 carbon atoms, —CN, —$CF_3$, —$C_2F_5$, —$C_3F_7$, —$NO_2$, —Y—$C_sH_{2s}$—R(18), phenyl, thienyl, furyl or a nitrogen-containing heterocycle having 1, 2, 3, 4, 5, 6, 7, 8 or 9 carbon atoms; where phenyl, thienyl, furyl and the nitrogen-containing heterocycle are unsubstituted or substituted by 1 or 2 substituents selected from the group consisting of F, Cl, Br, $CF_3$, $NO_2$, CN, $NH_2$, OH, methyl, ethyl, methoxy, dimethylamino, sulfamoyl, methylsulfonyl and methylsulfonylamino;
   Y is —O—, —CO—, —CO—O—, —O—CO—, —S—, —SO—, —$SO_2$—;
   s is zero, 1, 2, 3, 4, 5 or 6;
   R(18) is hydrogen, methyl, $CF_3$, $C_2F_5$, $C_3F_7$, cycloalkyl having 3, 4, 5 or 6 carbon atoms, —OR(21), —COOR(21), —NR(15a)R(16a), —CONR(15a)R(16a), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, $NH_2$, OH, methyl, ethyl, methoxy, dimethylamino, sulfamoyl, methylsulfonyl and methylsulfonylamino;
   R(15a) and R(16a) independently of one another are hydrogen or alkyl having 1, 2, 3 or 4 carbon atoms; or
   R(15a) and R(16a) together are a chain of 4 or 5 methylene groups of which one $CH_2$ group is unchanged or is replaced by —O—, —S—, —NH—, —N(CH$_3$)— or —N(benzyl)-;
   R(21) is alkyl having 1, 2 or 3 carbon atoms;

R(9) is hydrogen or together with R(2) is a bond;

X is —CR(22)R(23)—;
   R(22) and R(23) independently of one another are hydrogen, $CF_3$, alkyl having 1, 2 or 3 carbon atoms;

or their physiologically tolerable salts.

Very particular preference is given to compounds of the formula I in which:

R(1) is hydrogen;

R(2) is hydrogen or —OR(10a);
   R(10a) is hydrogen or methyl;

or

R(2) and R(9) together are a bond;

R(3) is R(10b)—$C_nH_{2n}$—,
   R(10b) is methyl;
   n is zero, 1 or 2;

R(4) is R(13)—$C_rH_{2r}$, where a $CH_2$ group of the $C_rH_{2r}$ group is unchanged or is replaced by —O—, —CO—O—, or —CONR(14)—;
   R(14) is hydrogen, alkyl having 1, 2 or 3 carbon atoms, —$C_yH_{2y}$—OR(12b);
   R(12b) is hydrogen, methyl or ethyl;
   y is 2 or 3;
   R(13) is $CH_3$, $CF_3$ or a nitrogen-containing heterocycle having 1, 2, 3, 4, 5, 6, 7, 8 or 9 carbon atoms, where the nitrogen-containing heterocycle is unsubstituted or substituted by 1 or 2 substituents selected from the group consisting of F, Cl, Br, $CF_3$, $NO_2$, CN, methyl or methoxy;
   r is zero, 1, 2, 3, 4, 5, 6, 7 or 8;

R(5), R(7) and R(8) are hydrogen;

R(6) is hydrogen, F, Cl, Br, alkyl having 1, 2, 3, 4 or 5 carbon atoms, cycloalkyl having 3, 4, 5 or 6 carbon atoms, —CN, —$CF_3$, —$C_2F_5$, —$C_3F_7$, —$NO_2$, —Y—$C_sH_{2s}$—R(18), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, methyl and methoxy;
   Y is —O—;
   s is 1, 2, 3, 4, 5 or 6;
   R(18) is hydrogen, $CF_3$, —OR(21), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, methyl and methoxy;
   R(21) is alkyl having 1, 2 or 3 carbon atoms;

R(9) is hydrogen or together with R(2) is a bond;

X is —CR(22)R(23)—;
   R(22) and R(23) independently of one another are $CF_3$ or methyl;

or their physiologically tolerable salts.

Specific preference is given to compounds of the formula I in which:

R(1) is hydrogen;

R(2) is hydrogen;

R(3) is methyl or ethyl;

R(4) is R(13)—$C_rH_{2r}$, where a $CH_2$ group of the $C_rH_{2r}$ group is unchanged or is replaced by —O—;

R(13) is $CH_3$ or $CF_3$;

r is zero, 1, 2, 3, 4, 5 or 6;

R(5), R(7) and R(8) are hydrogen;

R(6) is F, Cl, Br, alkyl having 1, 2, 3, 4 or 5 carbon atoms, —CN, —$CF_3$, —$NO_2$, —Y—$C_sH_{2s}$—R(18) or phenyl which is unsubstituted or substituted by 1 or 2 substituents selected from the group consisting of F, Cl, Br, $CF_3$, $NO_2$, CN, methyl and methoxy;

Y is —O—;

s is 1, 2, 3, 4, 5 or 6;

R(18) is hydrogen, $CF_3$ or phenyl, which is unsubstituted or substituted by 1 or 2 substituents selected from the group consisting of F, Cl, Br, $CF_3$, $NO_2$, CN, methyl and methoxy;

R(9) is hydrogen;

X is —CR(22)R(23)—;

R(22) and R(23) are methyl;

or their physiologically tolerable salts.

Specific preference is also given to compounds of the formula I in which:

R(1) is hydrogen;

R(2) is OH;

R(3) is methyl or ethyl;

R(4) is R(13)—$C_rH_{2r}$, where a $CH_2$ group of the $C_rH_{2r}$ group is unchanged or is replaced by —O—;

R(13) is $CH_3$ or $CF_3$;

r is zero, 1, 2, 3, 4, 5 or 6;

R(5), R(7) and R(8) are hydrogen;

R(6) is F, Cl, Br, alkyl having 1, 2, 3, 4 or 5 carbon atoms, —CN, —$CF_3$, —$NO_2$, —Y—$C_sH_{2s}$—R(18) or phenyl which is unsubstituted or substituted by 1 or 2 substituents selected from the group consisting of F, Cl, Br, $CF_3$, $NO_2$, CN, methyl and methoxy;

Y is —O—;

s is 1, 2, 3, 4, 5 or 6;

R(18) is hydrogen, $CF_3$ or phenyl, which is unsubstituted or substituted by 1 or 2 substituents selected from the group consisting of F, Cl, Br, $CF_3$, $NO_2$, CN, methyl and methoxy;

R(9) is hydrogen;

X is —CR(22)R(23)—;

R(22) and R(23) are methyl;

or their physiologically tolerable salts.

Specific preference is furthermore given to compounds of the formula I in which:

R(1) is hydrogen;

R(2) together with R(9) is a bond;

R(3) is methyl or ethyl;

R(4) is R(13)—$C_rH_{2r}$, where a $CH_2$ group of the $C_rH_{2r}$ group is unchanged or is replaced by —O—;

R(13) is $CH_3$ or $CF_3$;

r is zero, 1, 2, 3, 4, 5 or 6;

R(5), R(7) and R(8) are hydrogen;

R(6) is F, Cl, Br, alkyl having 1, 2, 3, 4 or 5 carbon atoms, —CN, —$CF_3$ or —$NO_2$, —Y—$C_sH_{2s}$—R(18) or phenyl which is unsubstituted or substituted by 1 or 2 substituents selected from the group consisting of F, Cl, Br, $CF_3$, $NO_2$, CN, methyl and methoxy;

Y is —O—;

s is 1, 2, 3, 4, 5 or 6;

R(18) is hydrogen, $CF_3$ or phenyl, which is unsubstituted or substituted by 1 or 2 substituents selected from the group consisting of F, Cl, Br, $CF_3$, $NO_2$, CN, methyl and methoxy;

X is —CR(22)R(23)—;

R(22) and R(23) are methyl;

or their physiologically tolerable salts.

Alkyl radicals and alkylene radicals may be straight-chain or branched. This option also applies to the alkylene radicals of the formulae $C_rH_{2r}$, $C_nH_{2n}$ and $C_sH_{2s}$. Alkyl radicals and alkylene radicals may also be straight-chain or branched if they are substituted or a part of other radicals, for example of an alkoxy radical or an alkylmercapto radical or a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, eicosyl. The divalent radicals which are derived from these radicals, for example methylene, 1,1-ethylene, 1,2-ethylene, 1,1-propylene 1,2-propylene, 2,2-propylene, 1,3-propylene, 1,4-butylene, 1,5-pentylene, 2,2-dimethyl-1,3-propylene, 1,6-hexylene, etc., are examples of alkylene radicals.

Nitrogen-containing heterocycles having 1, 2, 3, 4, 5, 6, 7, 8 or 9 carbon atoms are in particular the aromatic systems 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or 5-yl, 1,2,4-oxadiazol-3- or 5-yl, 1,3,4 -oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7-, or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl.

Particular preference is given to the nitrogen-containing heterocycles pyrrolyl, imidazolyl, quinolyl, pyrazolyl, pyridyl, pyrazinyl, pyrimidinyl and pyridazinyl.

Thienyl represents both 2- and 3-thienyl. Furyl represents 2- and 3-furyl.

Monosubstituted phenyl radicals may be substituted in the 2-, the 3- or the 4-position, disubstituted phenyl radicals may be substituted in the 2,3-, 2,4-, 2,5-, 2,6-, 3,4- or 3,5-position.

This substitution applies correspondingly in an analogous manner also to the nitrogen-containing heterocycles or to the thiophene radical.

If a radical is disubstituted, the substituents may be identical or different.

If R(2) and R(9) together are a bond, a 3H-indene skeleton is present if X is CR(22)R(23), or an indole, benzofuran or benzothiophene if X is NR(24), O or S. If R(10b) and R(11) together are a bond, the group R(10)—$C_nH_{2n}$—NR(11)— is preferably a nitrogen heterocycle which is attached via a nitrogen atom. If R(10) and R(11) together are a bond and the group R(10)—$C_nH_{2n}$—NR(11)— is a nitrogen heterocycle which is attached via a nitrogen atom, this nitrogen heterocycle is preferably a 4-membered ring or a ring which is larger than a 4-membered ring, for example a 5-membered ring, a 6-membered ring or a 7-membered ring.

If the compounds of the formula I contain one or more acidic or basic groups and/or one or more basic heterocycles, the invention relates also to the corresponding physiologically or toxicologically tolerable salts, in particular to the pharmaceutically acceptable salts. Thus, the compounds of the formula I which carry acidic groups, for example one or more COOH groups, can be used, for example, as alkali metal salts, preferably as sodium or potassium salts, or as alkaline earth metal salts, for example as calcium or magnesium salts, or as ammonium salts, for example as salts with ammonia or organic amines or amino acids. Compounds of the formula I which carry one or more basic, i.e. protonable, groups or contain one or more basic heterocyclic rings can also be used in the form of their physiologically acceptable acid addition salts with inorganic or organic acids, for example as hydrochlorides, phosphates, sulfates, methanesulfonates, acetates, lactates, maleates, fumurates, malates, gluconates, etc. If the compounds of the formula I contain acidic and basic groups in the same molecule, beside the salt forms described, the invention also includes internal salts, so-called betaines. Salts can be obtained from the compounds of the formula I by customary methods, for example by combination with an acid or base in a solvent or dispersant, or else by anion exchange from other salts.

When appropriately substituted, the compounds of the formula I can be present in stereoisomeric forms. If the compounds of the formula I contain one or more centers of asymmetry, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus relates to enantiomers, for example, in enantiomerically pure form, both as levo- and dextrorotatory antipodes, and also in the form of mixtures of the two enantiomers in different ratios or in the form of racemates. If cis/trans isomerism is present, the invention relates both to the cis form and to the trans form and to mixtures of these forms. The preparation of individual stereoisomers can be carried out, if desired, by resolution of a mixture according to customary methods or, for example, by stereoselective synthesis. If mobile hydrogen atoms are present, the invention also comprises all tautomeric forms of the compounds of the formula I.

The compounds of the formula I can be prepared by various chemical processes. Thus, a compound of the formula I is obtained, for example, by a) reacting a compound of the formula II,

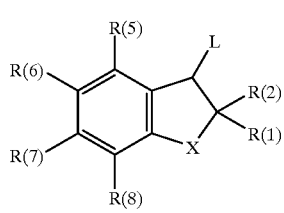

II in which R(1), R(2), R(5), R(6), R(7), R(8) and X are as defined above and L is a nucleofugic leaving group, in particular Cl, Br, I, methanesulfonyloxy, trifluoromethanesulfonyloxy or p-toluenesulfonyloxy, in a manner known per se with a sulfonamide or a salt thereof of the formula III

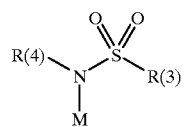

III in which R(3) and R(4) are as defined above and M is hydrogen or, preferably, a metal equivalent, particularly preferably lithium, sodium or potassium;

or by b) reacting a compound of the formula IV

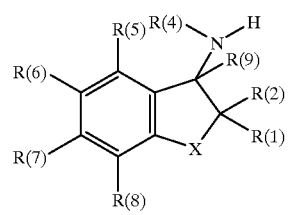

IV in which R(1), R(2), R(4), R(5), R(6), R(7), R(8), R(9) and X are as defined above with a sulfonic acid derivative of the formula V

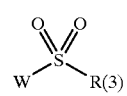

V in which R(3) is as defined above and W is a nucleofugic leaving group, such as, for example, fluorine, bromine, 1-imidazolyl, but in particular chlorine;

or by c) reacting a compound of the formula VI

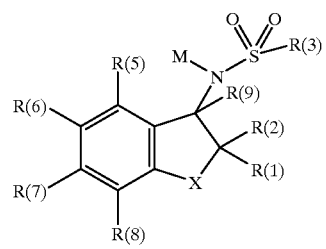

VI in which R(1), R(2), R(3), R(5), R(6), R(7), R(8), R(9), X and M are as defined above in a manner known per se in an alkylation reaction with an alkylating agent of the formula VII R(4)—L 

VII in which R(4) and L are as defined above; or by d) carrying out, in a compound of the formula I,

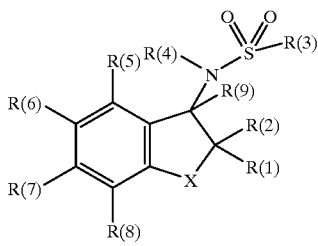

in which R(1) to R(9) and X are as defined above, in at least one of the positions R(5), R(6), R(7) and R(8) an electrophilic substitution reaction, if this position is hydrogen; or by e) reacting a compound of the formula VIII

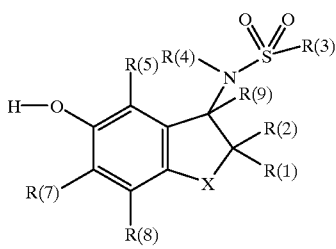

in which R(1), R(2), R(3), R(4), R(5), R(7), R(8), R(9) and X are as defined above with a compound of the formula R(18)—$C_sH_{2s}$—L, in which R(18), s and L are as defined above in an alkylation reaction;
or by f) reacting a compound of the formula IX,

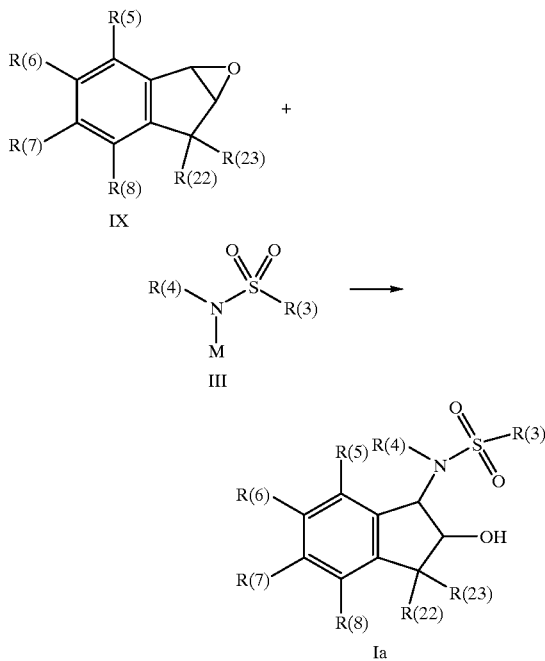

in which R(5), R(6), R(7), R(8), R(22) and R(23) are as defined above with a sulfonamide of the formula III in which R(3) and R(4) are as defined above and M is hydrogen or a metal equivalent, preferably lithium, sodium or potassium, or M is also advantageously a trialkylsilyl radical, for example a trimethylsilyl radical, to give a hydroxyindan of the formula Ia;
or by g) reacting a compound of the formula Ia with an alkylating agent of the formula R(10a)—L or an acylating agent of the formula $CH_3COL$ or an anhydride of the formula $(CH_3CO)_2O$, in which R(10a) and L are as defined above with the exception of hydrogen in a manner known per se in an alkylation or acylation reaction to give a compound of the formula Ib in which R(3), R(4), R(5), R(6), R(7), R(8), R(10a), R(22) and R(23) are as defined above;

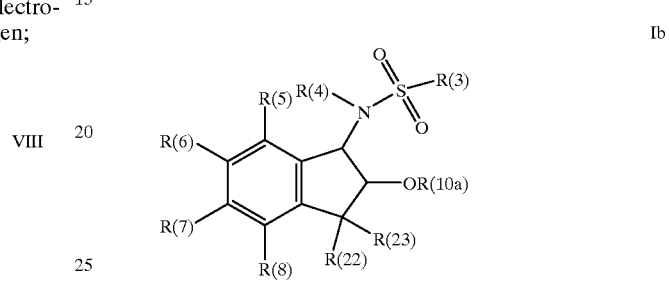

or by h) converting a compound of the formula Ia,

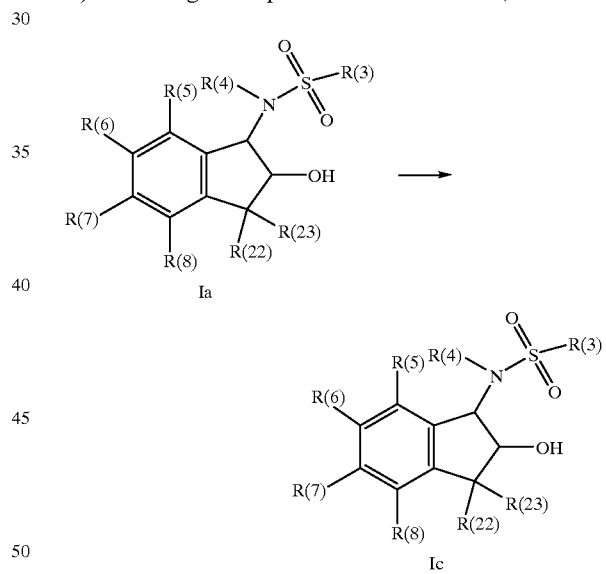

in which R(3), R(4), R(5), R(6), R(7), R(8), R(22) and R(23) are as defined above in an elimination reaction to give a compound of the formula Ic in which R(3), R(4), R(5), R(6), R(7), R(8), R(22) and R(23) are as defined above.

The procedure a) corresponds to the nucleophilic substitution of a leaving group in a reactive bicycle of the formula II by a sulfonamide or a salt thereof of the formula III. Owing to the higher nucleophilicity and higher reactivity of a sulfonamide which is present in salt form, it is preferred, when a free sulfonamide (formula III, M=H) is used, to initially generate a sulfonamide salt (formula III, M=metal cation) from this by action of a base. If a free sulfonamide (formula III, M=H) is used, the deprotonation of the sulfonamide to give the salt can be carried out in situ. Preference is given to using those bases which for their part are only alkylated to a small extent, if at all, such as, for example, sodium carbonate, potassium carbonate, sterically strongly hindered amines, for example dicyclohexylamine, N,N-dicyclohexylethylamine, or other strong nitrogen bases having low nucleophilicity, for example DBU (1,8-diazabicyclo[5.4.0]undec-7-ene) or N,N',N'"-triisopropylguanidine. However, it is also possible to employ other customarily used bases for the reaction, such as potassium tert-butoxide, sodium methoxide, alkali metal bicarbonates, alkali metal hydroxides, such as, for example, LiOH, NaOH or KOH, or alkaline earth metal hydroxides, such as, for example, $Ca(OH)_2$.

The reaction is preferably carried out in a solvent, particularly preferably in polar organic solvents, such as, for example, dimethylformamide (DMF), dimethylacetamide (DMA), dimethyl sulfoxide (DMSO), tetramethylurea (TMU), hexamethylphosphoric triamide (HMPT), tetrahydrofuran (THF), dimethoxyethane (DME) or other ethers, or, for example, also in a hydrocarbon, such as toluene, or in a halogenated hydrocarbon, such as chloroform or methylene chloride. However, it is also possible to carry out the reaction in polar protic solvents, such as, for example, water, methanol, ethanol or isopropanol. The reaction is preferably carried out in a temperature range of from −10 to +140° C., particularly preferably in the range of from 20 to 100° C. Conveniently, procedure a) can also be carried out under the conditions of a phase-transfer catalysis.

The compounds of the formula II are obtained by methods known from the literature, for example from the corresponding alcohols (formula II, L=—OH) by action of hydrogen halide HL (L=Cl, Br, I) or by action of an inorganic acyl halide ($POCl_3$, $PCl_3$, $PCl_5$, $SOCl_2$, $SOBr_2$) or by radical halogenation of the corresponding derivatives of the formula II in which L is hydrogen using halogenating agents which can be activated radically, such as N-bromosuccinimide (NBS) or $SO_2Cl_2$ (sulfuryl chloride), in the presence of a free-radical chain initiator, such as energy-rich light of the visible or ultraviolet frequency range, or by using a chemical free-radical initiator, such as azodiisobutyronitrile.

Procedure b)

describes the reaction, which is known per se and frequently used, of a reactive sulfonyl compound of the formula V, in particular of a chlorosulfonyl compound (W=Cl), with an amino derivative of the formula IV to give the corresponding sulfonamide derivative of the formula I.

The reaction is preferably carried out using a polar solvent, preferably in the presence of a base which can advantageously be used as a solvent itself, for example when using triethylamine, in particular pyridine and its homologues. Solvents likewise used are, for example, tetrahydrofuran, dioxane, dialkylated amides, such as DMF, DMA, and also TMU and HMPT. The reaction is in this case carried out at a temperature of from 0 to 160° C., preferably of from 20 to 100° C.

The amines of the formula IV are obtained in a manner known from the literature, preferably from the corresponding carbonyl compounds of the formula XX,

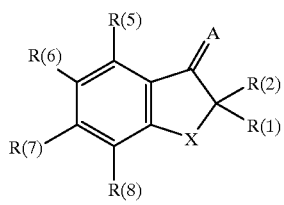

XX in which R(1), R(2), R(5), R(6), R(7), R(8) and X are as defined above and A is oxygen, either with ammonia or an amine of the formula XXI,

 XXI in which R(4) is as defined above, under reductive conditions or reductive catalytic conditions, preferably at elevated temperature and in an autoclave. In this case, Schiff bases of the formula XX in which A is R(4)—N= are initially formed by condensation reaction of the ketones of the formula XX (A=oxygen) and the amines of the formula XXI in situ, and the Schiff bases can be converted directly, i.e. without prior isolation, reductively into the amines of the formula IV. However, it is also possible to prepare the Schiff bases (formula XX, A is R(4)—N=), which are formed in the condensation reaction as intermediates from the compounds of the formulae XX and XXI, by methods known from the literature, and to isolate them first, to convert them then in a separate step using a suitable reducing agent, such as, for example, $NaBH_4$, $LiAlH_4$, $NaBH_3CN$ or by catalytic hydrogenation in the presence of, for example, Raney nickel or a noble metal, such as, for example, palladium, into the compounds of the formula IV.

The compounds of the formula IV in which R(4) is hydrogen can also be advantageously obtained in a manner known from the literature by reduction of oximes or oxime ethers (formula XX, A is =N—OR, R=H or alkyl) or hydrazones (formula XX, A is =N—$NR_2$, R for example=H or alkyl), for example using a complex metal hydride, or by catalytic hydrogenation. The oximes and hydrazones required for this purpose are preferably prepared in a manner known per se from the ketones of the formula XX (A=oxygen) using hydrazine or one of its derivatives or, for example, using hydroxylamine hydrochloride, under dehydrating conditions.

Particularly advantageously, the compounds of the formula IV in which R(4) is hydrogen can also be obtained by amination of ketones of the formula XX (A=oxygen) with a suitable ammonium compound, for example ammonium acetate, in the presence of a suitable reducing agent, such as, for example, $NaCNBH_3$ (J. Am. Chem. Soc. 93,1971, 2897).

The ketones of the formula XX (A=oxygen) are either known or can be prepared similarly to known methods. Some suitable ketones of the formula XX where X=CR(22)R(23) are described, for example, in J. Org. Chem. 19, 1954, 305 or Org. Prep. Proc. Int. 10, 1978, 123. Ketones of the formula XX in which X is oxygen are described, for example, in J. Org. Chem. 26, 1961, 4758 or Monatsh. Chem. 125, 1994, 971.

Alternatively, the amino derivatives of the formula IV can also be obtained in a manner known from the literature by reaction of the reactive compounds of the formula II where R(1), R(2), R(5), R(6), R(7), R(8), X and L are as defined above, either with ammonia or with an amine of the formula XXI where R(4) is as defined above.

Procedure c)
represents the alkylation reaction known per se of a sulfonamide or of one of its salts VI with an alkylating agent of the formula VII. In accordance with the analogy of the reaction to procedure a), the reaction conditions already described in detail under procedure a) apply to procedure c).

The preparation of the sulfonamide derivatives VI (where M=H) and their precursors have already been described in procedure b) where R(4) is then in each case hydrogen. The preparation of the alkylating agents VII is carried out according to analogous procedures in the literature or as described under procedure a), preferably from the corresponding hydroxyl compounds (formula VII where L equals —OH).

Procedure d)
describes the further chemical conversion of compounds of the formula I according to the invention into other compounds of the formula I by electrophilic substitution reactions in one or more of the positions designated by R(5) to R(8), which in each case are hydrogen. Preferred substitution reactions are
1. aromatic nitration to introduce one or more nitro groups, all or some of which may be reduced in subsequent reactions to amino groups. The amino groups, in turn, can be converted in subsequent reactions into other groups, for example in a Sandmeyer reaction, for example for introducing cyano groups;
2. aromatic halogenation, in particular for the introduction of chlorine, bromine or iodine;
3. chlorosulfonation, for example by the action of chlorosulfonic acid, for the introduction of a chlorosulfonyl group, which may be converted in subsequent reactions into other groups, for example into a sulfonamide group;
4. the Friedel-Crafts acylation reaction to introduce an acyl radical or a sulfonyl radical by action of the appropriate acyl chlorides in the presence of a Lewis acid as Friedel-Crafts catalyst, preferably in the presence of anhydrous aluminum chloride.

Procedure e)
describes the alkylation of a phenol of the formula VIII with an alkylating agent of the formula R(18)—$C_sH_{2s}$—L. To this end, the phenol is initially, by action of a suitable base, such as, for example, sodium hydride, converted into a phenolate salt, which is then reacted with the alkylating agent in a suitable polar solvent, such as, for example, dimethylformamide or dimethylacetamide, at temperatures between 20 and 150° C. The deprotonation of the alcohol to give the salt can also be carried out in situ, in which case the use of bases is preferred which for their part are not alkylated, such as, for example, potassium carbonate. Other suitable bases and solvents which can also be used are those which have already been mentioned under procedure a).

The phenols of the formula VIII are obtained by the methods described above under a) to c) or further below under f) to h); however, R(6) is then in each case OH or OR (R=suitable protective group, for example benzyl), and in the latter case a subsequent removal of the protective group is carried out.

Procedure f)
corresponds to the nucleophilic opening of an epoxide of the formula IX by a sulfonamide or a salt thereof of the formula III. If a free sulfonamide (formula III, M=H) is used, preference is given to initially generate a sulfonamide salt (formula III, M=metal cation) from this by action of a base, it being possible for the deprotonation of the sulfonamide to give the salt to be carried out in situ. Suitable for this purpose are the bases which have already been listed under procedure a).

The base can be employed in a stoichiometric amount or else catalytically. The use of the free sulfonamide in the presence of a small amount, for example 20%, of the corresponding sulfonamide sodium salt, which can be obtained from the sulfonamide, for example, by addition of 0.2 molar equivalents of sodium hydride, was found to be particularly advantageous.

The reaction is preferably carried out in a solvent, particularly preferably in polar organic solvents, such as, for example, dimethylformamide (DMF), dimethylacetamide (DMA), dimethyl sulfoxide (DMSO), tetramethylurea (TMU), hexamethylphosphoric triamide (HMPT), tetrahydrofuran (THF) or dimethoxyethane (DME). The reaction is preferably carried out in a temperature range of from −10 to +140° C., particularly preferably in the range of from 20 to 100° C.

Another preferred procedure for carrying out this reaction entails the use of sulfonamide derivatives of the formula III where M is a trialkylsilyl, for example a trimethylsilyl, radical. Here, it is advantageous to carry out the reaction in the presence of a fluoride, for example tetrabutylammonium fluoride.

The epoxides of the formula IX are obtained by methods known from the literature from the corresponding olefins of the formula XXII,

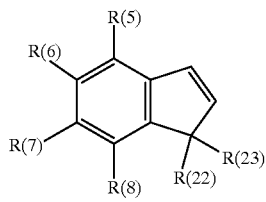

XXII where R(5), R(6), R(7), R(8), R(22) and R(23) are as defined above, for example by action of a suitable inorganic or organic peroxide, such as, for example, $H_2O_2$ or m-chloroperbenzoic acid, or by base-catalyzed cyclization of the corresponding bromohydrin, which can be obtained from XXII, for example, by reaction with N-bromosuccinimide and water. The epoxides of the formula IX can also be obtained in optically pure form from the olefins of the formula XXII, by oxidation in the presence of the chiral Jacobsen catalyst, such as described, for example, in Tetrahedron Letters 32, 1991, 5055. The olefins of the formula XXII can be obtained from the ketones of the formula XX (A=O, X=CR(22)R(23)) by reduction of the carbonyl group to an OH function, for example using sodium borohydride, and subsequent acid-catalyzed elimination, for example by heating with p-toluenesulfonic acid in toluene.

Procedure g)
describes the conversion of compounds of the formula Ia according to the invention into other compounds of the formula Ib according to the invention by alkylation or acylation of the 2-hydroxyl group. For the alkylation, the alcohol is initially converted into an alkoxide salt by action of a suitable base, such as, for example, sodium hydride, and the alkoxide salt is then reacted with the alkylating agent of the formula R(10a)—L in a suitable polar solvent, such as, for example, dimethylformamide, at temperatures between 20 and 150° C. The deprotonation of the alcohol to give the salt can also be carried out in situ, in which case preference is given to using bases which for their part are not alkylated, such as, for example, potassium carbonate. Other suitable bases and solvents which can also be used are those which have already been mentioned under procedure a). The acetylation of the compounds of the formula Ia is preferably carried out by reaction with acetic anhydride in a suitable polar solvent, such as pyridine or dimethylformamide, and, if appropriate, with addition of an acylation catalyst, such as, for example, dimethylaminopyridine.

Procedure h)

describes the conversion of a 2-hydroxyindan of the formula Ia into an indene of the formula Ic by elimination. To this end, the 2-hydroxyindan can either be directly subjected to a dehydrogenation in the presence of an acid or base, or it is possible to initially activate the hydroxyl group, for example by acetylation with acetic anhydride (see procedure g) or mesylation with methanesulfonyl chloride, which may be followed by a subsequent base-catalyzed elimination, for example by heating with DBU (1,8-diazabicyclo[5.4.0]undec-7-ene.

In all procedures, it may be appropriate to protect functional groups in the molecule temporarily in certain reaction steps. Such protective group techniques are familiar to the person skilled in the art. The choice of a protective group for groups in question and the methods for their introduction and removal are described in the literature and can be adapted to the individual case, where appropriate, without difficulties.

It has already been said that the compounds of the formula I surprisingly have a strong and specific blocking (closing) action on a $K^+$ channel which is opened by cyclic adenosine monophosphate (cAMP) and fundamentally differs from the well-known $K^+$ (ATP) channel, and that this $K^+$ (cAMP) channel identified in colonic tissue is very similar, perhaps even identical, to the $I_{K_s}$ channel identified in the cardiac muscle. For the compounds according to the invention, it was possible to show a strong blocking action on the $I_{K_s}$ channel in guinea-pig cardiomyocytes and on the $I_{sK}$ channel expressed in Xenopus oocytes. As a result of this blocking of the $K^+$ (cAMP) channel or of the $I_{K_s}$ channel, the compounds according to the invention display pharmacological actions of high therapeutic utility in the living body and are outstandingly suitable as pharmaceutical active compounds for the therapy and prophylaxis of various syndromes.

The compounds of the formula I according to the invention are thus distinguished as a novel active compound class of potent inhibitors of stimulated gastric acid secretion. The compounds of the formula I are thus useful pharmaceutical active compounds for the therapy and prophylaxis of ulcers of the stomach and of the intestinal region, for example of the duodenum. They are likewise suitable, on account of their strong gastric secretion-inhibiting action, as excellent therapeutics for the therapy and prophylaxis of reflux esophagitis.

The compounds of the formula I according to the invention are furthermore distinguished by an antidiarrheal action and are therefore suitable as pharmaceutical active compounds for the therapy and prophylaxis of diarrheal illnesses.

The compounds of the formula I according to the invention are furthermore suitable as pharmaceutical active compounds for the therapy and prophylaxis of cardiovascular disorders. In particular, they can be used for the therapy and prophylaxis of all types of arrhythmias, including atrial, ventricular and supraventricular arrhythmias, especially cardiac arrhythmias which can be eliminated by action-potential prolongation. They can be specifically used for the therapy and prophylaxis of atrial fibrillation and atrial flutters, and for the therapy and prophylaxis of reentry arrhythmias and for the prevention of sudden heart death as a result of ventricular fibrillation.

Although numerous substances having antiarrhythmic activity are already on the market, there is nevertheless no compound which is really satisfactory with respect to effectiveness, range of application and side-effect profile, so that there is furthermore a need for the development of improved antiarrhythmics.

The action of numerous known antiarrhythmics of the so-called class III is based on an increase in the myocardial refractory time by prolongation of the action potential duration. This is essentially determined by the extent of repolarizing $K^+$ streams which flow out of the cell via various $K^+$ channels. Particularly great importance is ascribed in this context to the so-called "delayed rectifier" $I_K$, of which two subtypes exist, a rapidly activated $I_{K_r}$ and a slowly activated $I_{K_s}$. Most known class III antiarrhythmics block $I_{K_r}$ predominantly or exclusively (e.g. dofetilide, d-sotalol). It has been shown, however, that these compounds have an increased proarrhythmic risk at low or normal heart rates, arrhythmias which are designated as "Torsades de pointes" in particular being observed (D. M. Roden; "Current Status of Class III Antiarrhythmic Drug Therapy"; Am. J. Cardiol. 72 (1993), 44B–49B). In the case of higher heart rates or stimulation of the β-receptors, however, the action potential-prolonging action of the $I_{K_r}$ blockers is markedly reduced, which is attributed to the fact that under these conditions the $I_{K_s}$ contributes more strongly to the repolarization. For these reasons, the substances according to the invention, which act as $I_{K_s}$ blockers, have significant advantages compared with the known $I_{K_r}$ blockers. In the meantime, it has also been described that a correlation exists between $I_{K_s}$ channel-inhibitory action and the suppression of life-threatening cardiac arrhythmias, such as are elicited, for example, by β-adrenergic hyperstimulation (e.g. T. J. Colatsky, C. H. Follmer and C. F. Starmer; "Channel Specificity in Antiarrhythmic Drug Action; Mechanism of potassium channel block and its role in suppressing and aggravating cardiac arrhythmias"; Circulation 82 (1990), 2235–2242; A. E. Busch, K. Malloy, W. J. Groh, M. D. Varnum, J. P. Adelman and J. Maylie; "The novel class III antiarrhythmics NE-10064 and NE-10133 inhibit $I_{sK}$ channels in Xenopus oocytes and $I_{K_s}$ in guinea pig cardiac myocytes"; Biochem. Biophys. Res. Commun. 202 (1994), 265–270).

Moreover, the compounds contribute to a marked improvement of cardiac insufficiency, in particular of congestive heart failure, advantageously in combination with contraction-promoting (positively inotropic) active compounds, e.g. phosphodiesterase inhibitors.

In spite of the therapeutically utilizable advantages which can be achieved by a blockade of the $I_{K_s}$, hitherto only very few compounds have been described which inhibit this subtype of the "delayed rectifier". The substance azimilide which is in development admittedly also has a blocking action on the $I_{K_s}$, but mainly blocks the $I_{K_r}$ (selectivity 1:10). WO-A-95/14470 claims the use of benzodiazepines as selective blockers of the $I_{K_s}$. Further $I_{K_s}$ blockers are described in FEBS Letters 396 (1996), 271–275: "Specific blockade of slowly activating $I_{sK}$ channels by chromanols . . . " and Pflügers Arch.—Eur. J. Physiol. 429 (1995), 517–530: "A new class of inhibitors of cAMP-mediated Cl-secretion in rabbit colon, acting by the reduction of cAMP-activated $K^+$ conductance".

The compounds of the formula I according to the invention and their physiologically tolerable salts can thus be used in animals, preferably in mammals, and in particular in humans as pharmaceuticals per se, in mixtures with one another or in the form of pharmaceutical preparations. The present invention also relates to the compounds of the formula I and their physiologically tolerable salts for use as pharmaceuticals, their use in the therapy and prophylaxis of the syndromes mentioned and their use for the production of medicaments therefor and of medicaments with K$^+$ channel-blocking action. Furthermore, the present invention relates to pharmaceutical preparations which contain an effective dose of at least one compound of the formula I and/or of a physiologically tolerable salt thereof in addition to customary, pharmaceutically innocuous excipients and auxiliaries. The pharmaceutical preparations normally contain 0.1 to 90 percent by weight of the compounds of the formula I and/or of their physiologically tolerable salts. The pharmaceutical preparations can be prepared in a manner known per se. For this purpose, the compounds of the formula I and/or their physiologically tolerable salts, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain compounds of the formula I according to the invention and/or their physiologically tolerable salts can be administered orally, parenterally, e.g. intravenously, rectally, by inhalation or topically, the preferred administration being dependent on the individual case, e.g. the particular course of the illness to be treated.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, agents for achieving a depot effect, buffer substances or colorants.

The compounds of the formula I can also be combined with other pharmaceutical active compounds to achieve an advantageous therapeutic effect. Thus in the treatment of cardiovascular disorders advantageous combinations with substances having cardiovascular activity are possible. Possible combination components of this type which are advantageous for cardiovascular disorders are, for example, other antiarrhythmics, i.e. class I, class II or class III antiarrhythmics, such as, for example $I_{Kr}$ channel blockers, e.g. dofetilide, or furthermore hypotensive substances such as ACE inhibitors (for example enalapril, captopril, ramipril), angiotensin antagonists, K$^+$ channel activators and also alpha- and beta-receptor blockers, but also sympathomimetic compounds and compounds having adrenergic activity, and also Na$^+$/H$^+$ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with H$_2$ antagonists (e.g. ranitidine, cimetidine, famotidine, etc.), in particular when used for the treatment of gastrointestinal disorders.

For an oral administration form, the active compounds are mixed with the additives suitable for this purpose, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. In this case the preparation can be carried out either as dry or as moist granules. Suitable oily excipients or solvents are, for example, vegetable or animal oils, such as sunflower oil or cod-liver oil. Suitable solvents for aqueous or alcoholic solutions are, for example, water, ethanol or sugar solutions or mixtures thereof. Further auxiliaries, also for other administration forms, are, for example, polyethylene glycols and polypropylene glycols.

For subcutaneous or intravenous administration, the active compounds, if desired with the substances customary for this such as solubilizers, emulsifiers or further auxiliaries, are brought into solution, suspension or emulsion. The compounds of the formula I and their physiologically tolerable salts can also be lyophilized and the lyophilizates obtained can be used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also additionally contain other pharmaceutical auxiliaries such as surfactants, emulsifiers and stabilizers as well as a propellant. Such a preparation contains the active compound customarily in a concentration from approximately 0.1 to 10, in particular from approximately 0.3 to 3, percent by weight.

The dose of the active compound of the formula I or of the physiologically tolerable salts thereof to be administered depends on the individual case and, as customary, is to be adapted for an optimum effect to the conditions of the individual case. Thus it depends, of course, on the frequency of administration and on the potency and duration of action of the compounds employed in each case for therapy or prophylaxis, but also on the nature and severity of the disease to be treated and on the sex, age, weight and individual responsiveness of the human or animal to be treated and on whether the therapy is acute or prophylactic. Customarily, the daily dose of a compound of the formula I in the case of administration to a patient approximately 75 kg in weight is 0.001 mg/kg of body weight to 100 mg/kg of body weight, preferably 0.01 mg/kg of body weight to 20 mg/kg of body weight. The dose can be administered in the form of an individual dose or divided into several, e.g. two, three or four, individual doses. In particular in the treatment of acute cases of cardiac arrhythmias, for example in an intensive care unit, parenteral administration by injection or infusion, e.g. by an intravenous continuous infusion, can also be advantageous.

The present invention is further illustrated by the following examples which are designed to teach those of ordinary skill in the art how to practice the invention. The following examples are merely illustrative of the invention and should not be construed as limiting the invention as claimed.

Experimental Part

List of Abbreviations

| | |
|---|---|
| DMF | N,N-dimethylformamide |
| EA | ethyl acetate |
| m.p. | melting point (unless stated otherwise, the melting points of the unpurified crude products are given; the melting points of the respective pure substances may be considerably higher) |
| RT | room temperature |
| TGF | tetrahydrofuran |

EXAMPLE 1

3,3-Dimethyl-1-(N-methyl-N-methylsulfonyl)aminoindan

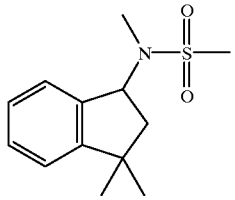

a) A solution of 25.0 g (0.156 mol) of 3,3-dimethylindan-1-one (Chem. Ber. 64, 1931, 1493) in 700 ml of methanol was stirred with 120.2 g (1.56 mol) of ammonium acetate and 69.1 g (1.1 mol) of sodium cyanoborohydride at 60° C. for 8 h. The reaction mixture was adjusted to pH<2 using dilute hydrochloric acid and concentrated using a rotary evaporator. The residue was taken up in dilute hydrochloric acid and extracted with EA, and the aqueous phase was then made alkaline using potassium carbonate solution and extracted with EA. The organic phase was dried with magnesium sulfate and concentrated under reduced pressure, giving 10.3 g of 1-amino-3,3-dimethylindan.

b) with ice-cooling, 4.0 g (34.7 mmol) of methanesulfonyl chloride were added dropwise to a solution of 5.1 g (31.6 mmol) of 1-amino-3,3-dimethylindan and 12.8 g (126.4 mmol) of triethylamine in 100 ml of THF. After 2 h at RT, 100 ml of water were added, the reaction mixture was concentrated to about 50 ml and admixed with 100 ml of water and the precipitate was filtered off with suction, rinsed with water and dried under reduced pressure. This procedure gave 6.7 g of 3,3-dimethyl-1-methylsulfonylaminoindan; m.p. 117–119° C.

c) A solution of 1.0 g (4.2 mmol) of 3,3-dimethyl-1-methylsulfonylaminoindan in 16 ml of DMF was added dropwise to a suspension of 0.15 g (5.1 mmol) of 80 percent sodium hydride in 10 ml of DMF, and the mixture was stirred at RT for 1 h. 0.59 g (4.2 mmol) of iodomethane was then added and the mixture was stirred at RT for another 3 h. After the addition of 3 ml of water, the reaction mixture was concentrated to dryness under reduced pressure, the residue was taken up in EA and water and the organic phase was washed with dilute hydrochloric acid and saturated sodium bicarbonate solution. Drying over magnesium sulfate and concentration gave 0.5 g of 3,3-dimethyl-1-(N-methyl-N-methylsulfonyl)aminoindan; m.p. 71–73° C.

EXAMPLE 2

3,3-Dimethyl-1-(N-ethylsulfonyl-N-methyl)aminoindan

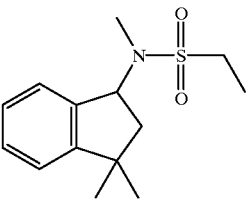

a) With ice-cooling, 4.44 g (34.7 mmol) of ethanesulfonyl chloride were added dropwise to a solution of 5.1 g (31.6 mmol) of 1-amino-3,3-dimethylindan (Example 1a) and 12.8 g (126 mmol) of triethylamine in 100 ml of THF. After 2 h at RT, the reaction mixture was concentrated under reduced pressure and the residue was taken up in water and EA. The organic phase was dried over magnesium sulfate and concentrated under reduced pressure, giving 6.4 g of 3,3-dimethyl-1-ethylsulfonylaminoindan.

b) A solution of 1.0 g (4.2 mmol) of 3,3-dimethyl-1-ethylsulfonylaminoindan in 16 ml of DMF was added dropwise to a suspension of 0.15 g (5.1 mmol) of 80 percent sodium hydride in 10 ml of DMF, and the mixture was stirred at RT for 1 h. 0.59 g (4.2 mmol) of iodomethane was added, and the mixture was stirred at RT for another 3 h. 3 ml of water were then added, the reaction mixture was concentrated to dryness using a rotary evaporator and the residue was taken up in EA and water. The organic phase was washed with dilute hydrochloric acid and saturated sodium bicarbonate solution, dried with magnesium sulfate and concentrated under reduced pressure. This procedure gave 0.9 g of 3,3-dimethyl-1-(N-methyl-N-ethylsulfonyl)aminoindan as an oil.

EXAMPLE 3

3,3-Dimethyl-1-(N-hexyl-N-methylsulfonyl)aminoindan

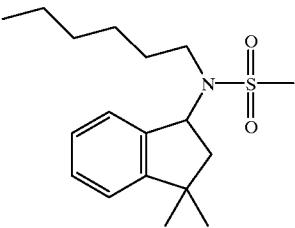

A solution of 1.0 g (4.2 mmol) of 3,3-dimethyl-1-methylsulfonylaminoindan (Example 1b) in 16 ml of DMF was added dropwise to a suspension of 0.15 g (5.1 mmol) of 80 percent sodium hydride in 10 ml of DMF, and the mixture was stirred at RT for 1 h. 0.89 g (4.2 mmol) of 1-iodohexane was added, and the mixture was stirred at RT for 3 h. 3 ml of water were then added, the reaction mixture was evaporated to dryness using a rotary evaporator and the residue was taken up in EA and water. The organic phase was washed with dilute hydrochloric acid and saturated sodium bicarbonate solution, dried with magnesium sulfate and concentrated using a rotary evaporator. This procedure gave 1.1 g of 3,3-dimethyl-1-(N-hexyl-N-methylsulfonyl) aminoindan as an oil.

$^1$H-NMR (200 MHz, CDCl$_3$): δ [ppm]=0.9 (t, 3H), 1.2 (s, 3H), 1.45 (s, 3H), 1.1–1.7 (m, 8H), 1.85 (dd, 1H), 2.25 (dd, 1H), 2.8–3.1 (m, 2H), 3.0 (s, 3H), 5.5 (t, 1H), 7.1–7.3 (m, 4H).

EXAMPLE 4

3,3-Dimethyl-1-(N-ethylsulfonyl-N-hexyl)aminoindan

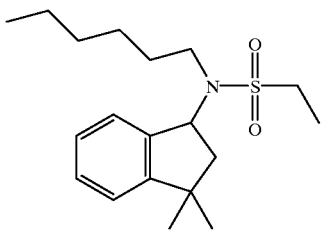

A solution of 1.0 g (4.0 mmol) of 3,3-dimethyl-1-ethylsulfonylaminoindan (Example 2a) in 16 ml of DMF was added dropwise to a suspension of 0.15 g (5.1 mmol) of 80 percent sodium hydride and 10 ml of DMF, and the mixture was stirred at RT for 1 h. 0.89 g (4.2 mmol) of 1-iodohexane was added and the mixture was stirred at RT for 3 h. 3 ml of water were then added, the reaction mixture was evaporated to dryness using a rotary evaporator and the residue was taken up in EA and water. The organic phase was washed with dilute hydrochloric acid and saturated sodium bicarbonate solution, dried with magnesium sulfate and concentrated using a rotary evaporator. This procedure gave 1.1 g of 3,3-dimethyl-1-(N-ethylsulfonyl-N-hexyl)aminoindan as an oil.

EXAMPLE 5

N-Butyl-N-(1,1-dioxo-2,3-dihydro-1H-benzo[b]thiophen-3-yl)-methanesulfonamide

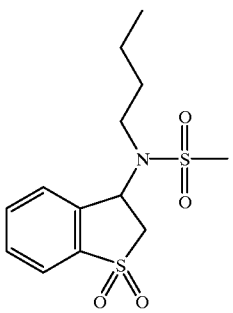

a) 9.0 g (54 mmol) of benzothiophene 1,1-dioxide and 7.9 g (108 mmol) of n-butylamine were suspended in 130 ml of ethanol, and the mixture was heated at reflux temperature for 3 h. The reaction mixture was concentrated under reduced pressure, giving 14.5 g of butyl-(1,1-dioxo-2,3-dihydro-1H-benzo[b]thiophen-3-yl)-amine as an oil.

b) 6.63 g (57 mmol) of methanesulfonyl chloride were added dropwise to a solution of 11.7 g (41 mmol) of butyl-(1,1-dioxo-2,3-dihydro-1H-benzo[b]thiophen-3-yl)-amine and 15.5 g (153 mmol) of triethylamine in 120 ml of THF, and the reaction mixture was stirred at RT overnight. Most of the THF was distilled off, the residue was diluted with 250 ml of water and the precipitate was filtered off with suction. Drying under reduced pressure gave 13.8 g of N-butyl-N-(1,1-dioxo-2,3-dihydro-1H-benzo[b]thiophen-3-yl)methanesulfonamide; m.p. 171–173° C.

EXAMPLE 6

N-Butyl-N-(6-nitro-1,1-dioxo-2,3-dihydro-1H-benzo[b]thiophen-3-yl)-methanesulfonamide

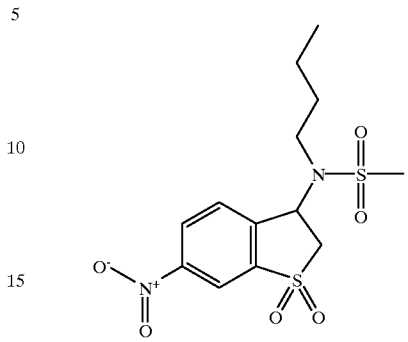

At −10° C., 0.5 g (1.6 mmol) of N-butyl-N-(1,1-dioxo-2,3-dihydro-1H-benzo[b]thiophen-3-yl)methanesulfonamide (Example 5) was dissolved in 5 ml of concentrated sulfuric acid and admixed with 0.15 g (1.8 mmol) of sodium nitrate, and the mixture was stirred at RT for 20 h. The reaction mixture was poured into 50 ml of ice-water, stirred for 30 minutes, filtered off with suction, washed neutral with water and dried under reduced pressure. This procedure gave 0.5 g of N-butyl-N-(6-nitro-1,1-dioxo-2,3-dihydro-1H-benzo[b]thiophen-3-yl)-methanesulfonamide; m.p. 52–55° C.

EXAMPLE 7

5-Fluoro-1-(N-methyl-N-methylsulfonyl)aminoindan

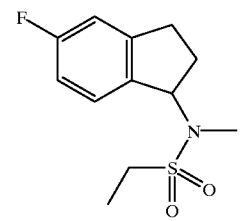

a) 4.5 g (30 mmol) of 5-fluoro-1-indanone and 20 ml of pyridine and 20 ml of ethanol were heated to 80° C. with 2.3 g (33 mmol) of hydroxylamine hydrochloride for 6 h. The solvents were distilled off, the residue was stirred with water and the precipitate was filtered off with suction and dried under reduced pressure. This procedure gave 4.8 g of 5-fluoro-1-indanoneoxime; m.p. 150–155° C.

b) 1.6 g of 5-fluoro-1-indanoneoxime in 30 ml of methanol were hydrogenated at atmospheric pressure and RT using Raney nickel as catalyst. The catalyst was filtered off, the solvent was removed under reduced pressure and the product was isolated as the hydrochloride by precipitation with etherial hydrochloric acid. This procedure gave 0.6 g of 5-fluoro-1-indanylamine hydrochloride; m.p. 245–247° C.

c) 0.6 g of 5-fluoro-1-indanylamine hydrochloride were reacted similarly to Example 2a to give 0.6 g of 5-fluoro-1-ethylsulfonylaminoindan.

d) Similarly to Example 2b, 0.6 g of 5-fluoro-1-ethylsulfonylaminoindan gave 0.42 g of 5-fluoro-1-(N-methyl-N-methylsulfonyl)aminoindan as an oil.

EXAMPLE 8
R-(+)-1-(N-Ethylsulfonyl-N-methyl)aminoindan

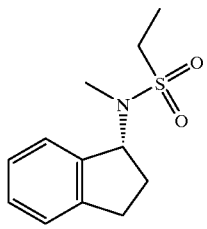

a) Similarly to Example 2b, 3 g of R-(−)-1-aminoindan gave 4.8 g of R-(+)-1-ethylsulfonylaminoindan; m.p. 66–71° C., optical rotation +27.9°.

b) Similarly to Example 2b, 1.12 g of R-(+)-1-ethylsulfonylaminoindan gave 0.87 g of R-(+)-1-(N-ethylsulfonyl-N-methyl)aminoindan as an oil; optical rotation +15.9°.

EXAMPLE 9
S-(−)-1-(N-Ethylsulfonyl-N-methyl)aminoindan

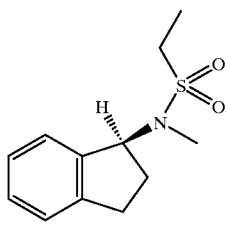

a) Similarly to Example 2b, 3 g of S-(+)-1-aminoindan gave 5.1 g of S-(−)-1-ethylsulfonylaminoindan; m.p. 64–68° C, optical rotation −29.5°.

b) Similarly to Example 2b, 1.12 g of S-(−)-1-ethylsulfonylaminoindan gave 0.89 g of S-(+)-1-(N-ethylsulfonyl-N-methyl)aminoindan as an oil; optical rotation +15.9°.

EXAMPLE 10
3,3-Dimethyl-6-nitro-1-(N-methyl-N-methylsulfonyl) aminoindan

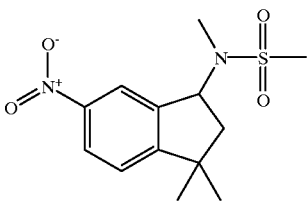

a) Similarly to Example 1a, reduction of 3,3-dimethyl-6-nitroindan-1-one (Org. Prep.Proced.Int. 10; 1978; 123) with sodium cyanoborohydride in the presence of ammonium acetate gave 1-amino-3,3-dimethyl-6-nitroindan.

b) Similarly to Example 1b, 1.5 g of 1-amino-3,3-dimethyl-6-nitroindan gave, by reaction with methanesulfonyl chloride, 1.5 g of 3,3-dimethyl-6-nitro-1-methylsulfonylaminoindan; m.p. 145–147° C.

c) A solution of 0.15 g (0.5 mmol) of 3,3-dimethyl-6-nitro-1-methylsulfonylaminoindan, 0.12 g (0.5 mmol) of tert-butyliminotris(dimethylamino)phosphorane (phosphazene base) and 0.08 g (0.55 mmol) of iodomethane in 4 ml of DMF was stirred at RT overnight. The solvent was distilled off and the residue was taken up in EA and washed twice with water. Drying over magnesium sulfate and concentration gave 0.15 g of 3,3-dimethyl-6-nitro-1-(N-methyl-N-methylsulfonyl)-aminoindan; m.p. 180–182° C.

EXAMPLE 11
3,3-Dimethyl-6-nitro-1-(N-butyl-N-methylsulfonyl) aminoindan

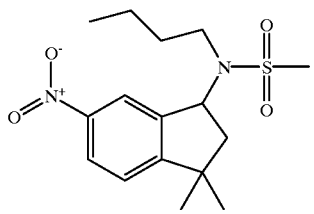

This compound was obtained by alkylation of 3,3-dimethyl-6-nitro-1-methylsulfonylaminoindan with 1-iodobutane similarly to Example 10c. M.p. 110–112° C.

EXAMPLE 12
3,3-Dimethyl-6-nitro-1-[N-(4-pyridylmethyl)-N-methylsulfonyl]aminoindan

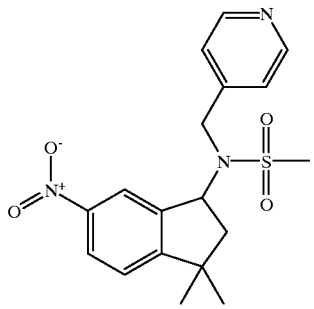

The compound was obtained by alkylation of 3,3-dimethyl-6-nitro-1-methylsulfonylaminoindan with 4-pyridylmethyl chloride hydrochloride similarly to Example 10c, but using double the molar amount of phosphazene base.

EXAMPLE 13
6-Butoxy-3,3-dimethyl-1-(N-methyl-N-methylsulfonyl) aminoindan

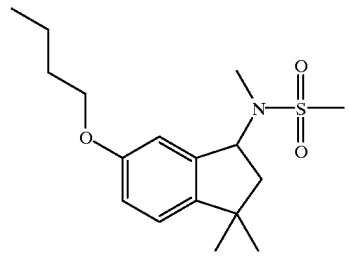

a) Under nitrogen, a solution of 28.5 g (0.16 mol) of 6-hydroxy-3,3-dimethylindan-1-one (J. Org. Chem. 19; 1954; 305) in 200 ml of DMF was added dropwise to a solution of 5.6 g (0.19 mol) of 80% sodium hydride in 250 ml of DMF. After 1 h at RT, 30.4 g (0.17 mol) of 1-iodobutane were added, and the mixture was stirred at RT for 2 h. The solvent was distilled off under reduced pressure, the residue was taken up in EA and water and the organic phase was washed successively with dil. hydrochloric acid and dil. sodium hydroxide solution. This procedure gave 31.3 g of 6-butoxy-3,3-dimethylindan-1-one.

b) A solution of 1.0 g (4.3 mmol) of 6-butoxy-3,3-dimethylindan-1 -one, 1.9 g (30 mmol) of sodium cyanoborohydride and 3.3 g (43 mmol) of ammonium acetate in 30 ml of methanol was heated at 60° C. for 5 h. Some water was added, and the methanol was then removed under reduced pressure and the residue was admixed with EA and hydrochloric acid. The acidic aqueous phase was separated off, made alkaline with aqueous sodium hydroxide solution and extracted with EA. This gave 0.4 g of 1-amino-6-butoxy-3,3-dimethylindan.

c) Similarly to Example 1b, 2.0 g of 1-amino-6-butoxy-3,3-dimethylindan gave 2.1 g of 6-butoxy-3,3-dimethyl-1-methylsulfonylaminoindan.

d) By alkylation of 0.5 g of 6-butoxy-3,3-dimethyl-1-methylsulfonylaminoindan with iodomethane similarly to Example 1c, 0.5 g of 6-butoxy-3,3-dimethyl-1-(N-methyl-N-methylsulfonyl)aminoindan was obtained as an oil.

EXAMPLE 14

6-Butoxy-3,3-dimethyl-1-(N-ethyl-N-methylsulfonyl) aminoindan

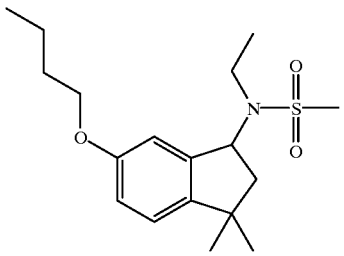

The compound was obtained as an oil by alkylation of 6-butoxy-3,3-dimethyl-1-methylsulfonylaminoindan (Example 13c) with iodoethane similarly to Example 1c.

$^1$H-NMR (CDCl$_3$): δ [ppm]=1.0 (t, 3H), 1.2 (s, 3H), 1.2 (t, 3H), 1.4 (s, 3H), 1.3–1.8 (m, 4H), 1.9 (dd, 1H), 2.25 (dd, 1H), 3.0 (s, 3H), 3.1 (m, 2H), 3.95 (t, 2H), 5.45 (dd, 1H), 6.8 (m, 2H), 7.05 (d, 1H).

Pharmacological Investigations

I$_{sK}$ channels from man, rat or guinea-pig were expressed in Xenopus oocytes. To do this, oocytes were first isolated from *Xenopus Laevis* and defolliculated. I$_{sK}$-encoding RNA synthesized in vitro was then injected into these oocytes. After I$_{sK}$ protein expression for 2–8 days, I$_{sK}$ currents were measured in the oocytes using the two microelectrode voltage clamp technique. The I$_{sK}$ channels were in this case as a rule activated using voltage jumps to –10 mV lasting 15 s. The bath was irrigated with a solution of the following composition: NaCl 96 mM, KCl 2 mM, CaCl$_2$ 1.8 mM, MgCl$_2$ 1 mM, HEPES 5 mM (titrated with NaOH to pH 7.5). These experiments were carried out at room temperature. The following were employed for acquiring data and analysis: Geneclamp amplifier (Axon Instruments, Foster City, U.S.A.) and MacLab D/A converter and software (ADInstruments, Castle Hill, Australia). The substances according to the invention were tested by adding them to the bath solution in different concentrations. The effects of the substances were calculated as the percentage inhibition of the I$_{sK}$ control current, which was obtained when no substance was added to the solution. The data were then extrapolated using the Hill equation in order to determine the inhibitory concentrations IC$_{50}$ for the respective substances.

REFERENCES

A. E. Busch, H.-G. Kopp, S. Waldegger, I. Samarzija, H. S üβbrich, G. Raber, K. Kunzelmann, J. P. Ruppersberg and F. Lang; "Inhibition of both exogenously expressed I$_{sK}$ and endogenous K$^+$ channels in Xenopus oocytes by isosorbiddinitrate"; J. Physiol. 491 (1995), 735–741;

T. Takumi, H. Ohkubo and S. Nakanishi; "Cloning of a membrane protein that induces a slow voltage-gated potassium current"; Science 242 (1989), 1042–1045;

M. D. Varnum, A. E. Busch, C. T. Bond, J. Maylie and J. P. Adelman; "The mink channel underlies the cardiac potassium current and mediates species-specific responses to protein kinase"; C. Proc. Natl. Acad. Sci. U.S.A. 90 (1993), 11528–11532.

In the described manner, using the human IsK protein, the following IC50 values were determined for the compounds according to the invention:

| Compound | IC-$_{50}$ [μM] |
|---|---|
| Example 2 | about 15 |
| Example 3 | <10 |
| Example 5 | >10 |
| Example 11 | 2.7 |
| Example 12 | about 2 |
| Example 13 | 1.2 |
| Example 14 | 0.44 |

The foregoing written description relates to various embodiments of the present invention. Numerous changes and modifications may be made therein without departing from the spirit and scope of the invention as defined in the following claims.

What is claimed is:

1. A compound of the formula I

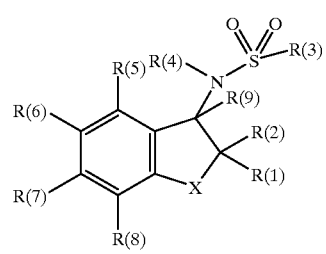

in which:

R(1) and R(2) independently of one another are hydrogen, CF$_3$, alkyl having 1, 2, 3, 4, 5 or 6 carbon atoms; or R(2) and R(9) together are a bond;

or R(2) is —OR(10a), if X is —CR(22)R(23)—;

R(10a) is hydrogen, acetyl or alkyl having 1, 2 or 3 carbon atoms;

R(3) is R(10b)—C$_n$H$_{2n}$—NR(11)— or R(10b)—C$_n$H$_{2n}$—, where a CH$_2$ group in the C$_n$H$_{2n}$ group is unchanged or is replaced by —O—, —CO—, —S—, —SO—, —SO$_2$— or —NR(12a)—;

R(12a) is hydrogen, methyl or ethyl;

R(10b) is methyl, cycloalkyl having 3, 4, 5, 6, 7 or 8 carbon atoms, CF$_3$, C$_2$F$_5$ or C$_3$F$_7$;

n is zero, 1, 2, 3, 4, 5, 6, 7, 8, 9 or 10;

R(11) is hydrogen or alkyl having 1, 2, 3, 4, 5 or 6 carbon atoms; or

R(10b) and R(11) together are a bond if n is greater than 2;

or

R(3) together with R(4) is an alkylene chain having 3, 4, 5, 6, 7 or 8 carbon atoms, where a $CH_2$ group of the alkylene chain is unchanged or is replaced by —O—, —CO—, —S—, —SO—, —$SO_2$— or —NR(12a)—;

R(12a) is hydrogen, methyl or ethyl;

R(4) is R(13)—$C_rH_{2r}$, where a $CH_2$ group of the $C_rH_{2r}$ group is unchanged or is replaced by —O—, —CH=CH—, —C≡C—, —CO—, —CO—O—, —O—CO—, —S—, —SO—, —$SO_2$—, —NR(14)— or —CONR(14)—;

R(14) is hydrogen, alkyl having 1, 2 or 3 carbon atoms, —$C_yH_{2y}$—OR(12b), —$C_yH_{2y}$—NR(12b)$_2$;

R(12b) is hydrogen, methyl or ethyl;

y is 2 or 3;

R(13) is $CH_3$, $CF_3$, $C_2F_5$, $C_3F_7$, cycloalkyl having 3, 4, 5, 6, 7 or 8 carbon atoms, —NR(15)R(16), —CONR(15)R(16), —OR(17), —COOR(17), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents, selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(15) and R(16) independently of one another are hydrogen or alkyl having 1, 2, 3 or 4 carbon atoms; or R(15) and R(16) together are a chain of 4 or 5 methylene groups of which a $CH_2$ group is unchanged or is replaced by —O—, —S—, —NH—, —N($CH_3$)— or —N(benzyl)-;

R(17) is hydrogen, alkyl having 1, 2 or 3 carbon atoms, —$C_zH_{2z}$OR(12c);

R(12c) is hydrogen, methyl or ethyl;

z is 2 or 3;

r is zero, 1, 2, 3, 4, 5, 6, 7, 8, 9, 10, 11, 12, 13, 14, 15, 16, 17, 18, 19 or 20;

R(5), R(6), R(7) and R(8) independently of one another are hydrogen, F, Cl, Br, I, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Y—$C_sH_{2s}$—R(18), phenyl, thienyl, furyl or a nitrogen-containing heterocycle having 1, 2, 3, 4, 5, 6, 7, 8 or 9 carbon atoms, where phenyl, thienyl, furyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Y is —O—, —CO—, —CO—O—, —O—CO—, —S—, —SO—, —$SO_2$—, —O—$SO_2$—, —$SO_2$NR(10c)— or —CONR(10c)—, where the link to the phenyl group is in each case effected through the atom on the left;

R(10c) is hydrogen or alkyl having 1, 2 or 3 carbon atoms;

s is zero, 1, 2, 3, 4, 5 or 6;

R(18) is hydrogen, methyl, $CF_3$, $C_2F_5$, $C_3F_7$, cycloalkyl having 3, 4, 5, 6, 7 or 8 carbon atoms, —OR(21), —COOR(21), —NR(15a)R(16a), —CONR(15a)R(16a), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(15a) and R(16a) independently of one another are hydrogen or alkyl having 1, 2, 3 or 4 carbon atoms; or R(15a) and R(16a) together are a chain of 4 or 5 methylene groups of which a $CH_2$ group is unchanged or is replaced by —O—, —S—, —NH—, —N($CH_3$)— or —N(benzyl)-;

R(21) is hydrogen or alkyl having 1, 2 or 3 carbon atoms;

R(9) is hydrogen or together with R(2) is a bond;

X is —CR(22)R(23)—;

R(22) and R(23) independently of one another are hydrogen, $CF_3$, alkyl having 1, 2, 3, 4, 5 or 6 carbon atoms;

or a physiologically tolerable salt thereof.

2. A compound of the formula I as claimed in claim 1 in which:

R(1) is hydrogen;

R(2) is hydrogen or —OR(10a);

R(10a) is hydrogen, acetyl or alkyl having 1, 2 or 3 carbon atoms;

or

R(2) and R(9) together are a bond;

R(3) is R(10b)—$C_nH_{2n}$—NR(11)— or R(10b)—$C_nH_{2n}$—, where a $CH_2$ group in the $C_nH_{2n}$ group is unchanged or is replaced by —O—, —CO—, —S—, —SO—, —$SO_2$— or —NR(12a)—;

R(12a) is hydrogen, methyl or ethyl;

R(10b) is methyl, cycloalkyl having 3, 4, 5, 6, 7 or 8 carbon atoms, $CF_3$, $C_2F_5$ or $C_3F_7$;

n is zero, 1, 2, 3, 4, 5, 6, 7, 8, 9 or 10;

R(11) is hydrogen or alkyl having 1, 2, 3, 4, 5 or 6 carbon atoms; or

R(10b) and R(11) together are a bond if n is greater than 2;

or

R(3) together with R(4) is an alkylene chain having 3, 4, 5, 6, 7 or 8 carbon atoms, where a $CH_2$ group of the alkylene chain is unchanged or is replaced by —O—, —CO—, —S—, —SO—, —$SO_2$— or —NR(12a)—;

R(12a) is hydrogen, methyl or ethyl;

R(4) is R(13)—$C_rH_{2r}$, where a $CH_2$ group of the $C_rH_{2r}$ group is unchanged or is replaced by —O—, —CH=CH—, —C≡C—, —CO—, —CO—O—, —O—CO—, —S—, —SO—, —$SO_2$—, —NR(14)— or —CONR(14)—;

R(14) is hydrogen, alkyl having 1, 2 or 3 carbon atoms, —$C_yH_{2y}$—OR(12b), —$C_yH_{2y}$—NR(12b)$_2$;

R(12b) is hydrogen, methyl or ethyl;

y is 2 or 3;

R(13) is $CH_3$, $CF_3$, $C_2F_5$, $C_3F_7$, cycloalkyl having 3, 4, 5, 6, 7 or 8 carbon atoms, —NR(15)R(16), —CONR(15)R(16), —OR(17), —COOR(17), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16) independently of one another are hydrogen or alkyl having 1, 2, 3 or 4 carbon atoms; or
R(15) and R(16) together are a chain of 4 or 5 methylene groups of which a $CH_2$ group is unchanged or is replaced by —O—, —S—, —NH—, —N($CH_3$)— or —N(benzyl)-;
R(17) is hydrogen, alkyl having 1, 2 or 3 carbon atoms, —$C_zH_{2z}$OR(12c);
R(12c) is hydrogen, methyl or ethyl;
z is 2 or 3;
r is zero, 1, 2, 3, 4, 5, 6, 7, 8, 9, 10, 11, 12, 13, 14, 15, 16, 17, 18, 19 or 20;
R(5), R(6), R(7) and R(8) independently of one another are hydrogen, F, Cl, Br, I, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Y—$C_sH_{2s}$—R(18), phenyl, thienyl, furyl or a nitrogen-containing heterocycle having 1, 2, 3, 4, 5, 6, 7, 8 or 9 carbon atoms, where phenyl, thienyl, furyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
Y is —O—, —CO—, —CO—O—, —O—CO—, —S—, —SO—, —$SO_2$—, —O—$SO_2$—, —$SO_2$NR(10c) or —CONR(10c)—, where the link to the phenyl group is in each case effected through the atom on the left;
R(10c) is hydrogen or alkyl having 1, 2 or 3 carbon atoms;
s is zero, 1, 2, 3, 4, 5 or 6;
R(18) is hydrogen, methyl, $CF_3$, $C_2F_5$, $C_3F_7$, cycloalkyl having 3, 4, 5, 6, 7 or 8 carbon atoms, —OR(21), —COOR(21), —NR(15 a)R(16a), —CONR(15a)R(16a), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15a) and R(16a) independently of one another are hydrogen or alkyl having 1, 2, 3 or 4 carbon atoms; or
R(15a) and R(16a) together are a chain of 4 or 5 methylene groups of which a $CH_2$ group is unchanged or is replaced by —O—, —S—, —NH—, —N($CH_3$)— or —N(benzyl)-;
R(21) is hydrogen or alkyl having 1, 2 or 3 carbon atoms;
R(9) is hydrogen or together with R(2) is a bond;
X is —CR(22)R(23)—;
R(22) and R(23) independently of one another are hydrogen, $CF_3$, alkyl having 1, 2, 3, 4, 5 or 6 carbon atoms,
or a physiologically tolerable salt thereof.

3. A compound of the formula I as claimed in claim 1 in which:
R(1) is hydrogen;
R(2) is hydrogen or —OR(10a);
R(10a) is hydrogen, acetyl or alkyl having 1, 2 or 3 carbon atoms; or
R(2) and R(9) together are a bond;
R(3) is R(10b)—$C_nH_{2n}$—,
R(10b) is methyl, cycloalkyl having 3, 4, 5 or 6 carbon atoms, $CF_3$, $C_2F_5$ or $C_3F_7$;
n is zero, 1, 2, 3, 4 or 5;
R(4) is R(13)—$C_rH_{2r}$, where a $CH_2$ group of the $C_rH_{2r}$ group is unchanged or is replaced by —O—, —CO—, —CO—O—, —O—CO—, —NR(14)— or —CONR(14)—;
R(14) is hydrogen, alkyl having 1, 2 or 3 carbon atoms, —$C_yH_{2y}$—OR(12b), —$C_yH_{2y}$—NR(12b)$_2$;
R(12b) is hydrogen, methyl or ethyl;
y is 2 or 3;
R(13) is $CH_3$, $CF_3$, $C_2F_5$, $C_3F_7$, cycloalkyl having 3, 4, 5 or 6 carbon atoms, —NR(15)R(16), —CONR(15)R(16), —OR(17), —COOR(17), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, $NH_2$, OH, methyl, ethyl, methoxy, dimethylamino, sulfamoyl, methylsulfonyl and methylsulfonylamino;
R(15) and R(16) independently of one another are hydrogen or alkyl having 1, 2, 3 or 4 carbon atoms; or
R(15) and R(16) together are a chain of 4 or 5 methylene groups of which a $CH_2$ group is unchanged or is replaced by —O—, —S—, —NH—, —N($CH_3$)— or —N(benzyl)-;
R(17) is hydrogen or alkyl having 1, 2 or 3 carbon atoms;
r is zero, 1, 2, 3, 4, 5, 6, 7, 8, 9 or 10;
R(5), R(6), R(7) and R(8) independently of one another are hydrogen, F, Cl, Br, alkyl having 1, 2, 3, 4 or 5 carbon atoms, cycloalkyl having 3, 4, 5 or 6 carbon atoms, —CN, —$CF_3$, —$C_2F_5$, —$C_3F_7$, —$NO_2$, —Y—$C_sH_{2s}$—R(18), phenyl, thienyl, furyl or a nitrogen-containing heterocycle having 1, 2, 3, 4, 5, 6, 7, 8 or 9 carbon atoms; where phenyl, thienyl, furyl and the nitrogen-containing heterocycle are unsubstituted or substituted by 1 or 2 substituents selected from the group consisting of F, Cl, Br, $CF_3$, $NO_2$, CN, $NH_2$, OH, methyl, ethyl, methoxy, dimethylamino, sulfamoyl, methylsulfonyl and methylsulfonylamino;
Y is —O—, —CO—, —CO—O—, —O—CO—, —S—, —SO—, —$SO_2$—;
s is zero, 1, 2, 3, 4, 5 or 6;
R(18) is hydrogen, methyl, $CF_3$, $C_2F_5$, $C_3F_7$, cycloalkyl having 3, 4, 5 or 6 carbon atoms, —OR(21), —COOR(21), —NR(15a)R(16a), —CONR(15a)R(16a), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, $NH_2$, OH, methyl, ethyl, methoxy, dimethylamino, sulfamoyl, methylsulfonyl and methylsulfonylamino;
R(15a) and R(16a) independently of one another are hydrogen or alkyl having 1, 2, 3 or 4 carbon atoms; or
R(15a) and R(16a) together are a chain of 4 or 5 methylene groups of which a $CH_2$ group is unchanged or is replaced by —O—, —S—, —NH—, —N($CH_3$)— or —N(benzyl)-;

R(21) is alkyl having 1, 2 or 3 carbon atoms;
R(9) is hydrogen or together with R(2) is a bond;
X is —CR(22)R(23)—;
R(22) and R(23) independently of one another are hydrogen, $CF_3$, alkyl having 1, 2 or 3 carbon atoms, or a physiologically tolerable salt thereof.

4. A compound of the formula I as claimed in claim 1, in which:
R(1) is hydrogen;
R(2) is hydrogen or —OR(10a);
R(10a) is hydrogen or methyl;
or
R(2) and R(9) together are a bond;
R(3) is R(10b)—$C_nH_{2n}$—,
R(10b) is methyl;
n is zero, 1 or 2;
R(4) is R(13)—$C_rH_{2r}$, where a $CH_2$ group of the $C_rH_{2r}$ group is unchanged or is replaced by —O—, —CO—O—, or —CONR(14)—;
R(14) is hydrogen, alkyl having 1, 2 or 3 carbon atoms, —$C_yH_{2y}$—OR(12b);
R(12b) is hydrogen, methyl or ethyl;
y is 2 or 3;
R(13) is $CH_3$, $CF_3$ or a nitrogen-containing heterocycle having 1, 2, 3, 4, 5, 6, 7, 8 or 9 carbon atoms, where the nitrogen-containing heterocycle is unsubstituted or substituted by 1 or 2 substituents selected from the group consisting of F, Cl, Br, $CF_3$, $NO_2$, CN, methyl and methoxy;
r is zero, 1, 2, 3, 4, 5, 6, 7 or 8;
R(5), R(7) and R(8) are hydrogen;
R(6) is hydrogen, F, Cl, Br, alkyl having 1, 2, 3, 4 or 5 carbon atoms, cycloalkyl having 3, 4, 5 or 6 carbon atoms, —CN, —$CF_3$, —$C_2F_5$, —$C_3F_7$, —$NO_2$, —Y—$C_sH_{2s}$—R(18), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, methyl and methoxy;
Y is —O—;
s is 1, 2, 3, 4, 5 or 6;
R(18) is hydrogen, $CF_3$, —OR(21), phenyl or a nitrogen-containing heterocycle having 1, 2, 3, 4, 5, 6, 7, 8 or 9 carbon atoms, where phenyl and the nitrogen-containing heterocycle are unsubstituted or substituted by 1 or 2 substituents selected from the group consisting of F, Cl, Br, $CF_3$, $NO_2$, CN, methyl and methoxy;
R(21) is alkyl having 1, 2 or 3 carbon atoms;
R(9) is hydrogen or together with R(2) is a bond;
X is —CR(22)R(23)—;
R(22) and R(23) independently of one another are $CF_3$ or methyl, or a physiologically tolerable salt thereof.

5. A compound of the formula I as claimed in claim 1, in which:
R(3) is methyl or;
R(2) is hydrogen;
R(3) is methyl or ethyl;
R(4) is R(13)—$C_rH_{2r}$, where a $CH_2$ group of the $C_rH_{2r}$ group is unchanged or is replaced by —O—;
R(13) is $CH_3$ or $CF_3$;
r is zero, 1, 2, 3, 4, 5 or 6;
R(5), R(7) and R(8) are hydrogen;
R(6) is F, Cl, Br, alkyl having 1, 2, 3, 4 or 5 carbon atoms, —CN, —$CF_3$, —$NO_2$, —Y—$C_sH_{2s}$—R(18) or phenyl which is unsubstituted or substituted by 1 or 2 substituents selected from the group consisting of F, Cl, Br, $CF_3$, $NO_2$, CN, methyl and methoxy;
Y is —O—;
s is 1, 2, 3, 4, 5 or 6;
R(18) is hydrogen, $CF_3$ or phenyl, which is unsubstituted or substituted by 1 or 2 substituents selected from the group consisting of F, Cl, Br, $CF_3$, $NO_2$, CN, methyl and methoxy;
R(9) is hydrogen;
X is —CR(22)R(23)—;
R(22) and R(23) are methyl, or a physiologically tolerable salt thereof.

6. A compound of the formula I as claimed in claim 1, in which:
R(1) is hydrogen;
R(2) is OH;
R(3) is methyl or ethyl;
R(4) is R(13)—$C_rH_{2r}$, where a $CH_2$ group of the $C_rH_{2r}$ group is unchanged or is replaced by —O—;
R(13) is $CH_3$ or $CF_3$;
r is zero, 1, 2, 3, 4, 5 or 6;
R(5), R(7) and R(8) are hydrogen;
R(6) is F, Cl, Br, alkyl having 1, 2, 3, 4 or 5 carbon atoms, —CN, —$CF_3$, —$NO_2$, —Y—$C_sH_{2s}$, —R(18) or phenyl which is unsubstituted or substituted by 1 or 2 substituents selected from the group consisting of F, Cl, Br, $CF_3$, $NO_2$, CN, methyl and methoxy;
Y is —O—;
s is 1, 2, 3, 4, 5 or 6;
R(18) is hydrogen, $CF_3$ or phenyl, which is unsubstituted or substituted by 1 or 2 substituents selected from the group consisting of F, Cl, Br, $CF_3$, $NO_2$, CN, methyl and methoxy;
R(9) is hydrogen;
X is —CR(22)R(23)—;
R(22) and R(23) are methyl, or a physiologically tolerable salt thereof.

7. A compound of the formula I as claimed in claim 1, in which:
R(1) is hydrogen;
R(2) together with R(9) is a bond;
R(3) is methyl or ethyl;
R(4) is R(13)—$C_rH_{2r}$, where a $CH_2$ group of the $C_rH_{2r}$ group is unchanged or is replaced by —O—;
R(13) is $CH_3$ or $CF_3$;
r is zero, 1, 2, 3, 4, 5 or 6;
R(5), R(7) and R(8) are hydrogen;
R(6) is F, Cl, Br, alkyl having 1, 2, 3, 4 or 5 carbon atoms, —CN, —$CF_3$, —$NO_2$, —Y—$C_sH_{2s}$—R(18) or phenyl which is unsubstituted or substituted by 1 or 2 substituents selected from the group consisting of F, Cl, Br, $CF_3$, $NO_2$, CN, methyl and methoxy;
Y is —O—;
s is 1, 2, 3, 4, 5 or 6;
R(18) is hydrogen, $CF_3$ or phenyl, which is unsubstituted or substituted by 1 or 2 substituents selected from the group consisting of F, Cl, Br, $CF_3$, $NO_2$, CN, methyl and methoxy;

X is —CR(22)R(23)—;
R(22) and R(23) are methyl,
or a physiologically tolerable salt thereof.

8. A pharmaceutical composition comprising an effective amount of a compound of the formula I as claimed in claim 1 as active compound, together with a pharmaceutically acceptable carrier.

9. A pharmaceutical composition as claimed in claim 8 together with one or more other pharmacologically active compounds.

10. A method for the therapeutic treatment and prophylaxis of a $K^+$ channel-mediated disease which comprises administering to a mammal an effective amount of a compound of the formula I as claimed in claim 1.

11. A method for the inhibition of gastric acid secretion which comprises administering to a mammal an effective amount of a compound of the formula I as claimed in claim 1.

12. A method for the therapeutic treatment or prophylaxis of an ulcer of the stomach or of the intestinal region which comprises administering to a mammal an effective amount of a compound of the formula I as claimed in claim 1.

13. A method for the therapeutic treatment or prophylaxis of reflux esophagitis which comprises administering to a mammal an effective amount of a compound of the formula I as claimed in claim 1.

14. A method for the therapeutic treatment or prophylaxis of a diarrheal illness which comprises administering to a mammal an effective amount of a compound of the formula I as claimed in claim 1.

15. A method for the therapeutic treatment or prophylaxis of an arrhythmia which comprises administering to a mammal an effective amount of a compound of the formula I as claimed in claim 1.

16. A method for the therapeutic treatment or prophylaxis of an arrhythmia as claimed in claim 15 wherein said arrhythmia is atrial, ventricular or supraventricular.

17. A method for the therapeutic treatment or prophylaxis of a cardiac arrhythmia which comprises administering to a mammal an effective amount of a compound of the formula I as claimed in claim 1.

18. A method for the therapeutic treatment or prophylaxis of a cardiac arrhythmia as claimed in claim 17 wherein said cardiac arrhythmia is eliminated by action potential prolongation.

19. A method for the therapeutic treatment or prophylaxis of an atrial fibrillation or an atrial flutter which comprises administering to a mammal an effective amount of a compound of the formula I as claimed in claim 1.

20. A method for the therapeutic treatment or prophylaxis of a reentry arrhythmia which comprises administering to a mammal an effective amount of a compound of the formula I as claimed in claim 1.

21. A method for the therapeutic treatment and prophylaxis of sudden heart death as a result of ventricular fibrillation which comprises administering to a mammal an effective amount of a compound of the formula I as claimed in claim 1.

22. A method for the therapeutic treatment of cardiac insufficiency which comprises administering to a mammal an effective amount of a compound of the formula I as claimed in claim 1.

23. A pharmaceutical composition comprising an effective amount of a compound of the formula I as claimed in claim 1 and a beta-adrenergic receptor blocker as active compounds, together with a pharmaceutically acceptable carrier.

* * * * *

UNITED STATES PATENT AND TRADEMARK OFFICE
CERTIFICATE OF CORRECTION

PATENT NO.: 6,015,822

DATED: January 18, 2000

INVENTORS: Joachim BRENDEL et al.

It is certified that an error appears in the above-identified patent and that said Letters Patent is hereby corrected as shown below:

Claim 5, Column 35, line 60, "R(3) is methyl or," should read --R(1) is hydrogen--.

Claim 6, Column 36, line 31, "— Y —$C_sH_{2s'}$— R(18)" should read

-- —Y —$C_sH_{2s}$—R(18)--.

Signed and Sealed this

Third Day of October, 2000

*Attest:*

Q. TODD DICKINSON

*Attesting Officer*   *Director of Patents and Trademarks*